(12) United States Patent
Fuchs et al.

(10) Patent No.: US 9,523,104 B2
(45) Date of Patent: Dec. 20, 2016

(54) PROCESSES AND SYSTEMS FOR THE PRODUCTION OF ALCOHOLS

(71) Applicant: BUTAMAX ADVANCED BIOFUELS LLC, Wilmington, DE (US)

(72) Inventors: Benjamin Fuchs, Wilmington, DE (US); Brian Michael Roesch, Middletown, DE (US); Mathias E. Stolarski, Swarthmore, PA (US); James Gregory Wood, Newark, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 133 days.

(21) Appl. No.: 14/203,809

(22) Filed: Mar. 11, 2014

(65) Prior Publication Data

US 2014/0273127 A1    Sep. 18, 2014

Related U.S. Application Data

(60) Provisional application No. 61/777,103, filed on Mar. 12, 2013.

(51) Int. Cl.
| | | |
|---|---|---|
| *C12N 9/28* | (2006.01) | |
| *C12P 7/16* | (2006.01) | |
| *C12P 7/10* | (2006.01) | |
| *C12P 7/06* | (2006.01) | |

(52) U.S. Cl.
CPC .. *C12P 7/10* (2013.01); *C12P 7/06* (2013.01); *C12P 7/16* (2013.01); *Y02E 50/10* (2013.01); *Y02E 50/17* (2013.01)

(58) Field of Classification Search
CPC ..................................... C12N 9/28; C12P 7/16
See application file for complete search history.

(56) References Cited

U.S. PATENT DOCUMENTS

| | | | |
|---|---|---|---|
| 4,491,522 A | 1/1985 | Ishida et al. | |
| 4,865,973 A | 9/1989 | Kollerup et al. | |
| 5,221,357 A | 6/1993 | Brink | |
| 5,514,583 A | 5/1996 | Picataggio et al. | |
| 5,712,133 A | 1/1998 | Picatagglio et al. | |
| 6,509,051 B1 | 1/2003 | Wills | |
| 6,660,506 B2 | 12/2003 | Nguyen et al. | |
| 6,703,227 B2 | 3/2004 | Jackel et al. | |
| 6,732,454 B2 | 5/2004 | Anderson et al. | |
| 6,766,595 B2 | 7/2004 | Anderson | |
| 6,996,917 B2 | 2/2006 | Anderson | |
| 7,083,954 B2 | 8/2006 | Jackel et al. | |
| 7,148,366 B2 | 12/2006 | Cheryan | |
| 7,223,575 B2 | 5/2007 | Zhang et al. | |
| 7,241,256 B2* | 7/2007 | Cornay | B01J 19/1806 494/31 |
| 7,455,997 B2 | 11/2008 | Hughes | |
| 7,481,890 B2 | 1/2009 | Cheryan | |
| 7,608,729 B2 | 10/2009 | Winsness et al. | |
| 7,666,282 B2 | 2/2010 | Sylvester et al. | |
| 7,741,119 B2 | 6/2010 | Viitanen et al. | |
| 7,851,188 B2 | 12/2010 | Donaldson et al. | |
| 7,888,082 B2 | 2/2011 | Verser et al. | |
| 8,192,627 B2 | 6/2012 | Gallop et al. | |
| 8,373,008 B2 | 2/2013 | Grady et al. | |
| 8,373,009 B2 | 2/2013 | Grady et al. | |
| 8,409,834 B2 | 4/2013 | Burlew et al. | |
| 8,426,173 B2 | 4/2013 | Bramucci et al. | |
| 8,426,174 B2 | 4/2013 | Bramucci et al. | |
| 8,460,439 B2 | 6/2013 | Parten | |
| 8,476,047 B2 | 7/2013 | Burlew et al. | |
| 8,557,540 B2* | 10/2013 | Burlew | B01D 3/002 426/656 |
| 8,563,788 B2 | 10/2013 | Grady et al. | |
| 8,569,552 B2 | 10/2013 | Grady et al. | |
| 8,574,406 B2 | 11/2013 | Grady et al. | |
| 8,617,861 B2 | 12/2013 | Grady et al. | |
| 8,628,643 B2 | 1/2014 | Grady et al. | |
| 8,697,404 B2 | 4/2014 | Anton et al. | |
| 8,759,044 B2 | 6/2014 | DiCosimo et al. | |
| 8,765,425 B2 | 7/2014 | DiCosimo et al. | |
| 8,828,695 B2 | 9/2014 | Grady et al. | |
| 8,845,506 B2* | 9/2014 | Walraven | B04B 1/20 494/53 |
| 8,865,443 B2 | 10/2014 | Burlew et al. | |
| 8,906,204 B2 | 12/2014 | Xu | |
| 8,968,522 B2 | 3/2015 | Xu et al. | |
| 8,968,523 B2 | 3/2015 | Xu et al. | |

(Continued)

FOREIGN PATENT DOCUMENTS

| | | |
|---|---|---|
| DE | 102006040567 | 3/2008 |
| WO | 9528476 | 10/1995 |

(Continued)

OTHER PUBLICATIONS

Davison, et al., Continuous Direct Solvent Extraction of Butanol in a Fermenting Fluidized-Bed Bioreactor with Immobilized Clostridium acetobutylicum, Appl. Biochem. Biotechnol. 39/40:415-426, 1993.
Feldmann, et al., Pentose Metabolism in Zymomonas Mobilis Wild-type and Recombinant Strains, Appl. Microbiol. Biotechnol., 38:354-361, 1992.
Hahnai, et al., Engineered synthetic Pathway for Isopropanol Production in *Escherichia coli*, Appl. Environ. Microbiol., 73:7814-7818, 2007.
Lynd, Microbial Cellulose Utilization: Fundamentals and Biotechnology, Microbiol. Mol. Biol. Rev., 66:506-577, 2002.
Methods in Yeast Genetics, 2005 Cold Spring Harbor Laboratory Press, Cold Spring Harbor, NY, pp. 201-202.
Ohta, et al., Genetic Improvement of *Escherichia coli* for Ethanol Production: Chromosomal Integration of Zymomonas Mobilis Genes Encoding Pyruvate Decarboxylase and Alcohol dehydrogenase II, Appl. Environ. Microbiol. 57:893-900, 1991.
Shen, et al., Metabolic Engineering of *Escherichia coli* for 1-Butanol and 1-Propanol Production via the Keto-acid Pathways, Metabol. Eng., 10:312-320, 2008.

(Continued)

*Primary Examiner* — Karen Cochrane Carlson
*Assistant Examiner* — Natalie Moss

(57) ABSTRACT

The present invention relates to processes and systems for the production of fermentative products such as ethanol and butanol. The present invention also provides methods for separating feed stream components for improved biomass processing productivity.

49 Claims, 12 Drawing Sheets

(56) References Cited

U.S. PATENT DOCUMENTS

| | | |
|---|---|---|
| 8,969,055 B2 | 3/2015 | Grady et al. |
| 2005/0272134 A1 | 12/2005 | Hughes |
| 2006/0173169 A1 | 8/2006 | Cheryan |
| 2007/0014905 A1 | 1/2007 | Chen et al. |
| 2007/0031918 A1 | 2/2007 | Dunson, Jr. et al. |
| 2007/0092957 A1 | 4/2007 | Donaldson et al. |
| 2008/0032344 A1 | 2/2008 | Fallavollita |
| 2008/0121742 A1 | 5/2008 | Foster |
| 2008/0261230 A1 | 10/2008 | Liao et al. |
| 2008/0274526 A1 | 11/2008 | Bramucci et al. |
| 2009/0029432 A1 | 1/2009 | Abbas et al. |
| 2009/0061490 A1 | 3/2009 | Edwards et al. |
| 2009/0163376 A1 | 6/2009 | Li et al. |
| 2009/0171129 A1 | 7/2009 | Evanko et al. |
| 2009/0176286 A1 | 7/2009 | O'Connor et al. |
| 2009/0181153 A1 | 7/2009 | Bendorf et al. |
| 2009/0203099 A1 | 8/2009 | Caimi et al. |
| 2009/0209009 A1 | 8/2009 | Tolan et al. |
| 2009/0246846 A1 | 10/2009 | Viitanen et al. |
| 2009/0259078 A1 | 10/2009 | Schucker |
| 2009/0269823 A1 | 10/2009 | Bramucci et al. |
| 2009/0305363 A1 | 12/2009 | Anthony et al. |
| 2009/0305370 A1 | 12/2009 | Grady et al. |
| 2010/0058649 A1 | 3/2010 | Bootsma |
| 2010/0081154 A1 | 4/2010 | Flint et al. |
| 2010/0092603 A1 | 4/2010 | Brunsma et al. |
| 2010/0143995 A1 | 6/2010 | Erdner-Tindall et al. |
| 2010/0144001 A1 | 6/2010 | Horton |
| 2010/0196980 A1 | 8/2010 | Smith et al. |
| 2010/0197519 A1 | 8/2010 | Li et al. |
| 2010/0273228 A1 | 10/2010 | Sant'Anna et al. |
| 2010/0319424 A1 | 12/2010 | Wietgrefe |
| 2011/0008863 A1 | 1/2011 | Zhu et al. |
| 2011/0097773 A1 | 4/2011 | Grady et al. |
| 2011/0124060 A1 | 5/2011 | Anthony et al. |
| 2011/0136193 A1 | 6/2011 | Grady et al. |
| 2011/0244536 A1 | 10/2011 | Nagarajan et al. |
| 2011/0294179 A1 | 12/2011 | Grady et al. |
| 2011/0312044 A1 | 12/2011 | Anton et al. |
| 2011/0312053 A1 | 12/2011 | Burlew et al. |
| 2012/0015416 A1 | 1/2012 | Anthony et al. |
| 2012/0051980 A1 | 3/2012 | Gallop et al. |
| 2012/0156738 A1 | 6/2012 | Anton et al. |
| 2012/0196332 A1 | 8/2012 | Muniglia et al. |
| 2012/0208246 A1 | 8/2012 | Anton et al. |
| 2012/0237988 A1 | 9/2012 | Anthony et al. |
| 2012/0322117 A1 | 12/2012 | Anton et al. |
| 2012/0323047 A1 | 12/2012 | Dauner et al. |
| 2013/0164795 A1 | 6/2013 | Lowe et al. |
| 2013/0165678 A1 | 6/2013 | Kohl et al. |
| 2013/0217060 A1 | 8/2013 | Bramucci et al. |
| 2013/0224728 A1 | 8/2013 | Bramucci et al. |
| 2013/0252297 A1 | 9/2013 | Parten |
| 2013/0295661 A1 | 11/2013 | Roesch et al. |
| 2013/0309738 A1 | 11/2013 | Barr et al. |
| 2014/0018581 A1 | 1/2014 | Grady et al. |
| 2014/0024064 A1 | 1/2014 | Burlew et al. |
| 2014/0073021 A1 | 3/2014 | Bazzana et al. |
| 2014/0073820 A1 | 3/2014 | Bazzana et al. |
| 2014/0093931 A1 | 4/2014 | Dauner et al. |
| 2014/0094630 A1 | 4/2014 | Anton et al. |
| 2014/0099688 A1 | 4/2014 | Grady et al. |
| 2014/0106419 A1 | 4/2014 | Bazzana et al. |
| 2014/0142352 A1 | 5/2014 | Dauner et al. |
| 2014/0162344 A1 | 6/2014 | DiCosimo et al. |
| 2014/0178529 A1 | 6/2014 | Anton et al. |
| 2014/0234929 A1 | 8/2014 | Barr et al. |
| 2014/0256020 A1 | 9/2014 | DiCosimo et al. |
| 2014/0273130 A1 | 9/2014 | Anthony et al. |
| 2014/0303408 A1 | 10/2014 | Zaher et al. |
| 2014/0311889 A1 | 10/2014 | Zaher et al. |
| 2014/0363865 A1 | 12/2014 | Burlew et al. |
| 2015/0010975 A1 | 1/2015 | Burlew et al. |
| 2015/0010984 A1 | 1/2015 | Bhalla et al. |
| 2015/0060259 A1 | 3/2015 | Xu |

FOREIGN PATENT DOCUMENTS

| | | |
|---|---|---|
| WO | 2008025522 | 3/2008 |
| WO | 2008086115 | 7/2008 |
| WO | 2009015333 | 1/2009 |
| WO | 2009026706 | 3/2009 |
| WO | 2009149270 | 10/2009 |
| WO | 2010059919 | 5/2010 |
| WO | 2010075241 | 7/2010 |
| WO | 2010096002 | 8/2010 |
| WO | 2011020082 | 2/2011 |
| WO | 2011159962 | 12/2011 |
| WO | 2011159967 | 12/2011 |
| WO | 2011160030 | 12/2011 |
| WO | 2012036857 | 5/2012 |
| WO | 2013166458 | 11/2013 |

OTHER PUBLICATIONS

Underwood, et al., Flux through Citrate synthase Limits the Growth of Ethanologenic *Escherichia coli* KO11 during Xylose Fermentation, Appl. Environ. Microbiol. 68:1071-1081, 2002.

Zhang, et al., Metabolic Engineering of a Pentose Metabolism Pathway in Ethanologenic Zymomonas Mobilis, Science 267:240-243, 1995.

Singh, et al., Extraction of Oil from Corn Distillers Dried Grains with Solubles, Transactions of the ASAE, 41:1775-1777, 1998.

Gunt Hamburg, Thermal Processing Engineering, p. 1, 2009.

Ohgren, et al., Simultaneous saccharification and co-fermentation of glucose and xylose in steam-pretreated corn stover at high fiber content with *Saccharomyces cerevisiae* TMB3400, J. Biotechnol. 126:488-498, 2006.

Kotrba, Encouraging Numbers for Corn Oil Feedstock, Biodiesel Magazine, Jun. 22, 2010, pp. 1-2.

Eysenbach, et al. Pretreatment of Industrial Wastes, Manual of Practice No. FD-3, Water Environment Federation, Alexandria, VA, 1994, p. 95.

U.S. Appl. No. 14/415,928, filed Jan. 20, 2015 (Butamax).

U.S. Appl. No. 14/428,731, filed Mar. 20, 2015 (Butamax).

International Search Report and Written Opinion of corresponding PCT/US2014/022926; mailed Jun. 17, 2014.

\* cited by examiner

PROCESSES AND SYSTEMS FOR THE PRODUCTION OF ALCOHOLS

This application claims the benefit of U.S. Provisional Application No. 61/777,103, filed Mar. 12, 2013; the entire contents of which are herein incorporated by reference.

FIELD OF THE INVENTION

The present invention relates to processes and systems for the production of fermentative products such as ethanol and butanol. The present invention also provides methods for separating feed stream components for improved biomass processing productivity.

BACKGROUND OF THE INVENTION

Alcohols have a variety of industrial and scientific applications such as fuels, reagents, and solvents. For example, butanol is an important industrial chemical and drop-in fuel component with a variety of applications including use as a renewable fuel additive, a feedstock chemical in the plastics industry, and a food-grade extractant in the food and flavor industry. Accordingly, there is a high demand for alcohols such as butanol as well as for efficient and environmentally-friendly production methods including, for example, fermentation processes and the use of biomass as feedstock for these processes.

Biomass may be derived from a variety of biological materials such as plants (e.g., corn and sugar cane crops), and cellulosic and lignocellulosic sources. For some production processes such as fermentation, biomass may be treated to generate a fermentable carbon source (e.g., sugars), oil, and undissolved solids which may be added directly to a fermentor. However, the undissolved solids and oil may interfere with the recovery of the fermentative products. For example, the presence of undissolved solids and oil in the fermentation broth may decrease the mass transfer coefficient of a recovery method such as liquid-liquid extraction. In addition, for a method such as liquid-liquid extraction, the presence of the undissolved solids and oil may impede phase separation, may result in the accumulation of oil in the extractant leading to reduced extraction efficiency, may slow the disengagement of extractant droplets from the fermentation broth, and may increase the loss of extractant due to trapping in the undissolved solids.

In addition, removal of oil may also provide beneficial effects on the production of fermentative products as well as commercial benefits. For example, some oils such as corn oil and soybean oil may be used as a feedstock for biodiesel and thus, provide an additional revenue stream for alcohol producers. In addition, removing oil can result in energy savings for the production facility due to more efficient fermentation, decreased equipment fouling, and decreased energy requirements, for example, the energy needed to dry distillers grains.

Thus, there is a continuing need to develop more efficient processes and systems for producing fermentative products such as product alcohols (e.g., ethanol, butanol) using fermentation processes. The present invention satisfies this need and provides processes and systems for producing product alcohols by separating feed stream components prior to the fermentation process and therefore, controlling the amount of undissolved solids and/or oil entering the fermentation process.

SUMMARY OF THE INVENTION

The present invention relates to processes and systems for separating feed stream components and controlling the amount of undissolved solids and/or oil in a feed stream for the production of fermentative alcohols such as ethanol and butanol. The separated components provide a mechanism for increasing biomass processing productivity including, in particular, improving fermentation co-product profiles. By separating the feed streams into certain components including, for example, (1) an aqueous stream comprising carbohydrate or carbon source, (2) a feed stream comprising oil, and (3) a feed stream comprising undissolved solids, the components may be re-combined in a controlled, optimized manner, or removed from the process or system for other uses. The present invention also relates to processes and systems for removing oil from a fermentor feed stream in the production of fermentative alcohols such as ethanol and butanol. In some embodiments, undissolved solids and oil may be removed from a fermentor feed stream.

The present invention is directed to a method for producing product alcohol comprising: providing a feedstock slurry comprising fermentable carbon source, undissolved solids, and oil; separating at least a portion of the feedstock slurry forming (i) an aqueous solution comprising fermentable carbon source, (ii) a wet cake comprising solids, and (iii) an oil stream; wherein the step of separating at least a portion of the feedstock slurry includes using a three-phase centrifuge to separate the feedstock slurry; and adding the aqueous solution to a fermentation broth comprising microorganisms in a fermentor whereby a product alcohol is produced. In some embodiments, the three-phase centrifuge may comprise an overflow mechanism. In some embodiments, the overflow mechanism may be adjustable. In some embodiments, the overflow mechanism may be a weir. In some embodiments, the overflow mechanism may be used for discharging the oil stream and/or the aqueous solution. In some embodiments, the three-phase centrifuge may comprise a pressure discharge mechanism. In some embodiments, the pressure discharge mechanism may be adjustable. In some embodiments, the pressure discharge mechanism may be selected from the group consisting of a dip tube and an impeller. In some embodiments, the pressure discharge mechanism may be used for discharging the oil stream and/or the aqueous solution. In some embodiments, the three-phase centrifuge may comprise an overflow mechanism and a pressure discharge mechanism. In some embodiments, one or more control parameters of the three-phase centrifuge may be adjusted to improve separation of the feedstock slurry. In some embodiments, the one or more control parameters may be selected from differential speed, bowl speed, flow rate, impeller position, weir position, scroll pitch, residence time, and discharge volume. In some embodiments, the oil stream may be separated from the feedstock slurry intermittently or in batch mode. In some embodiments, at least a portion of the oil stream may be returned to the three-phase centrifuge. In some embodiments, the oil stream may be combined with feedstock slurry to form a mixture of oil and feedstock slurry, and the mixture may be returned to the three-phase centrifuge. In some embodiments, the method further may comprise the step of washing the wet cake to recover oil and fermentable sugars. In some embodiments, the wet cake may be washed with water, hexane, isobutanol, isohexane, ethanol, petroleum distillates, or mixtures thereof. In some embodiments, the water may be fresh water, backset, cook water, process water, lutter water, evaporation water, or combinations thereof. In some embodiments, the washing step may be repeated two or more times. In some embodiments, the method may further comprise recombining at least a portion of the aqueous solution with at least a portion of the wet cake to form a mixture of wet cake and aqueous solution; and adding the mixture to the fermentation broth. In some embodiments, the product alcohol may be methanol, ethanol, propanol, butanol, pentanol, and isomers thereof. In some embodiments, butanol may be 1-butanol, 2-butanol, or isobutanol. In some embodiments, feedstock slurry may comprise oil in an amount that is less than about two volume percent (2 vol %) of the feedstock slurry. In some embodiments, feedstock slurry may comprise oil in an amount that is less than about 1.5 volume percent (1.5 vol %) of the feedstock slurry. In some embodiments, feedstock slurry may comprise oil in an amount that is less than about one volume percent (1 vol %) of the feedstock slurry. In some embodiments, the feedstock may be rye, wheat, corn, corn mash, cane, cane mash, barley, cellulosic material, lignocellulosic material, or mixtures thereof. In some embodiments, the method may further comprise separating the aqueous solution forming (i) a second aqueous solution comprising fermentable carbon source, (ii) a second wet cake comprising solids, and (iii) a second oil stream. In some embodiments, the aqueous solution may be separated by decanter bowl centrifugation, three-phase centrifugation, disk stack centrifugation, filtering centrifugation, decanter centrifugation, filtration, microfiltration, vacuum filtration, beltfilter, pressure filtration, membrane filtration, crossflow filtration, drum filter, filtration using a screen, screen separation, rotary screen, grating, porous grating, flotation, hydrocyclone, filter press, screwpress, gravity settler, or vortex separator.

The present invention is also directed to a method to improve oil recovery from a feedstock slurry comprising providing a feedstock slurry comprising fermentable carbon source, undissolved solids, and oil; separating at least a portion of the feedstock slurry forming (i) an aqueous solution comprising fermentable carbon source, (ii) a wet cake comprising solids, and (iii) an oil stream; and returning at least a portion of the oil stream to the feedstock slurry; wherein an increased concentration of oil in the feedstock slurry improves the recovery of oil from the feedstock slurry. The present invention is also directed to a method for modifying the moisture content of undissolved solids comprising providing a feedstock slurry comprising fermentable carbon source, undissolved solids, and oil; separating at least a portion of the feedstock slurry forming (i) an aqueous solution comprising fermentable carbon source, (ii) a wet cake comprising undissolved solids, and (iii) an oil stream; wherein the step of separating at least a portion of the feedstock slurry includes using a three-phase centrifuge to separate the feedstock slurry; and adjusting the residence time of the three-phase centrifuge; wherein the moisture content of the wet cake is modified by adjusting the residence time of the three-phase centrifuge. The present invention is directed to a method of improving the separation of liquid phases comprising providing a feedstock slurry comprising fermentable carbon source, undissolved solids, and oil; separating at least a portion of the feedstock slurry forming (i) a first liquid phase comprising an aqueous solution, (ii) a second liquid phase comprising oil, and (iii) a wet cake comprising undissolved solids; wherein the step of separating at least a portion of the feedstock slurry includes using a three-phase centrifuge to separate the feedstock slurry and the three-phase centrifuge comprises a weir; and adjusting the weir of the three-phase centrifuge; wherein the levels of the two liquid phases are modified by adjusting the weir thereby providing improved separation of the two liquid phases. The various embodiments described herein may be applicable to all methods, processes, and systems described herein.

The present invention is also directed to a method for producing product alcohol comprising providing a feedstock; liquefying the feedstock to create a feedstock slurry, wherein the feedstock slurry comprises fermentable carbon source, undissolved solids, and oil; separating at least a portion of the feedstock slurry forming (i) an aqueous solution comprising fermentable carbon source, (ii) a wet cake comprising solids, and (iii) an oil stream; wherein the step of separating at least a portion of the feedstock slurry includes conducting the feedstock slurry to a three-phase centrifuge and using the three-phase centrifuge to separate the feedstock slurry; contacting the aqueous solution with a fermentation broth comprising microorganisms in a fermentor; fermenting the fermentable carbon source in the fermentor to produce product alcohol. In some embodiments, the feedstock may be corn and the oil may be corn oil. The various embodiments described herein may be applicable to all methods, processes, and systems described herein.

In some embodiments, the microorganism may be a recombinant microorganism. In some embodiments, the microorganism may comprise a butanol biosynthetic pathway. In some embodiments, butanol may be isobutanol.

The present invention is also directed to a system for producing product alcohol comprising one or more liquefaction vessels configured to liquefy a feedstock to create a feedstock slurry; one or more three-phase centrifuges configured to separate feedstock slurry forming (i) an aqueous solution comprising fermentable carbon source, (ii) a wet cake comprising solids, and (iii) an oil stream; and one or more fermentors configured to ferment the aqueous solution to produce product alcohol. In some embodiments, the three-phase centrifuge may comprise an inlet for receiving feedstock slurry; a first outlet for discharging aqueous solution, a second outlet for discharging wet cake; and a third outlet for discharging an oil. In some embodiments, the system may comprise two or more three-phase centrifuges. In some embodiments, the system may further comprise one or more saccharification vessels configured to saccharify the sugar in the feedstock slurry.

DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

DESCRIPTION OF THE INVENTION

Figure 1:
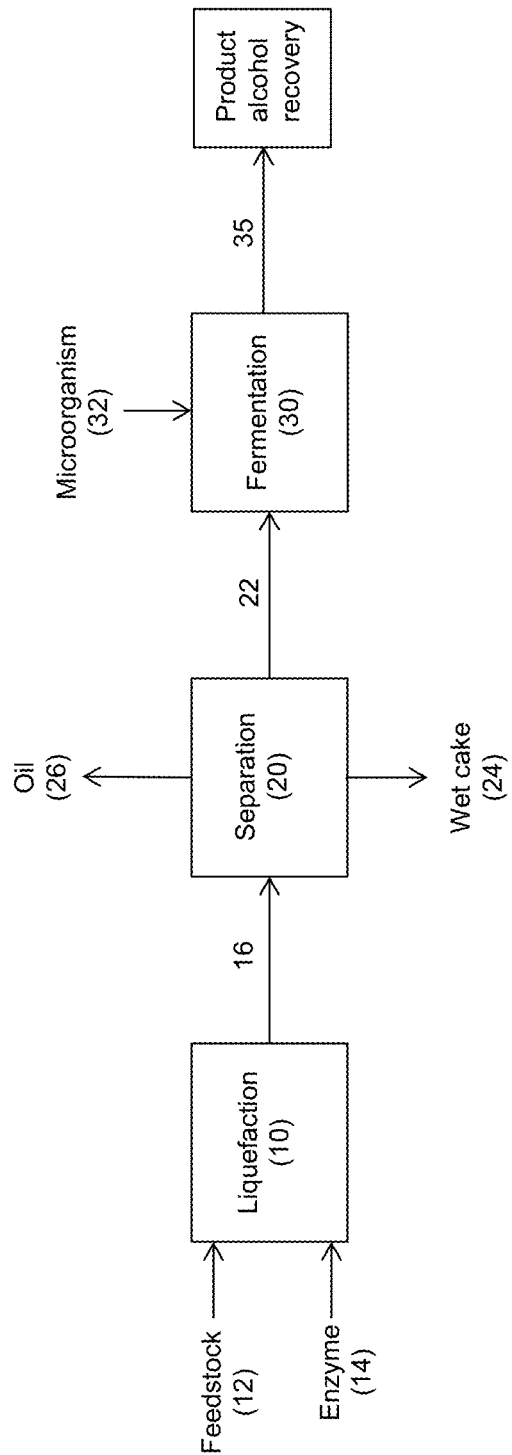
FIG. 1 schematically illustrates an exemplary process and system of the present invention, in which undissolved solids (e.g., wet cake) and oil are removed from feedstock slurry.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents, and other references mentioned herein are incorporated by reference in their entireties for all purposes.

In order to further define this invention, the following terms and definitions are herein provided.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, that is, occurrences of the element or component. Therefore, "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

"Biomass" as used herein refers to a natural product containing hydrolyzable polysaccharides that provide fermentable sugars including any sugars and starch derived from natural resources such as corn, sugar cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components such as protein and/or lipids. Biomass may be derived from a single source or biomass may comprise a mixture derived from more than one source. For example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste (e.g., forest thinnings). Examples of biomass include, but are not limited to, corn grain, corn cobs, crop residues such as corn husks, corn stover, grasses, wheat, rye, wheat straw, spelt, triticale, barley, barley straw, oats, hay, rice, rice straw, switchgrass, potato, sweet potato, cassava, Jerusalem artichoke, waste paper, sugar cane bagasse, sorghum, sugar cane, sugar beet, fodder beet, soy, palm, coconut, rapeseed, safflower, sunflower, millet, eucalyptus, miscanthus, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing biomass for purposes of fermentation such as by milling, treating, and/or liquefying, and treated biomass may comprise fermentable sugar and may comprise water. For example, cellulosic and/or lignocellulosic biomass may be processed to obtain a hydrolysate containing fermentable sugars by any method known to one skilled in the art. A low ammonia pretreatment is disclosed in U.S. Patent Application Publication No. 2007/0031918A1, which is herein incorporated by reference. Enzymatic saccharification of cellulosic and/or lignocellulosic biomass typically makes use of enzyme mixtures for hydrolysis of cellulose and hemicellulose to produce a hydrolysate containing sugars including glucose, xylose, and arabinose. Saccharification enzymes suitable for cellulosic and/or lignocellulosic biomass are reviewed in Lynd, et al. (Microbiol. Mol. Biol. Rev. 66:506-577, 2002).

"Fermentable carbon source" or "fermentable carbon substrate" as used herein refers to a carbon source capable of being metabolized by microorganisms. Suitable fermentable carbon sources include, but are not limited to, monosaccharides such as glucose or fructose; disaccharides such as lactose or sucrose; oligosaccharides; polysaccharides such as starch or cellulose; one carbon substrates; and mixtures thereof.

"Fermentable sugar" as used herein refers to one or more sugars capable of being metabolized by microorganisms for the production of fermentative products such as alcohols.

"Feedstock" as used herein refers to a feed in a fermentation process, the feed containing a fermentable carbon source with or without undissolved solids and oil, and where applicable, the feed containing a fermentable carbon source before or after the fermentable carbon source has been liberated from starch or obtained from the hydrolysis of complex sugars by further processing such as by liquefaction, saccharification, or other process. Feedstock includes or may be derived from a biomass. Suitable feedstocks include, but are not limited to, rye, wheat, corn, corn mash, cane, cane mash, barley, cellulosic material, lignocellulosic material, or mixtures thereof. Where reference is made to "feedstock oil," it will be appreciated that the term encompasses the oil produced from a given feedstock.

"Fermentation broth" as used herein refers to the mixture of water, fermentable carbon sources (e.g., sugars, starch), dissolved solids, and optionally microorganisms producing alcohol, product alcohol, undissolved solids, and all other constituents of the material in which product alcohol is being made by the metabolism of fermentable carbon sources by the microorganisms to form alcohol, water, and carbon dioxide ($CO_2$). From time to time as used herein, the term "fermentation medium" and "fermented mixture" may be used synonymously with "fermentation broth."

"Fermentor" or "fermentation vessel" as used herein refers to a vessel, unit, or tank in which the fermentation reaction is carried out whereby product alcohol such as ethanol or butanol is made from fermentable carbon sources. Fermentor may also refer to a vessel, unit, or tank in which growth of microorganisms occurs. In some instances, both microbial growth and fermentation may occur in a fermentor. The term "fermentor" may be used synonymously herein with "fermentation vessel."

"Saccharification vessel" as used herein refers to a vessel, unit, or tank in which saccharification (i.e., the hydrolysis of oligosaccharides to monosaccharides) is carried out. Where fermentation and saccharification occur simultaneously, the saccharification vessel and the fermentor may be the same vessel.

"Saccharification enzyme" refers to one or more enzymes that are capable of hydrolyzing polysaccharides and/or oligosaccharides, for example, alpha-1,4-glucosidic bonds of glycogen, or starch. Saccharification enzymes may include enzymes capable of hydrolyzing cellulosic or lignocellulosic materials as well.

"Liquefaction vessel" as used herein refers to a vessel, unit, or tank in which liquefaction is carried out. Liquefaction is the process in which oligosaccharides are released from the feedstock. In embodiments where the feedstock is corn, oligosaccharides are released from the corn starch content during liquefaction.

"Sugar" as used herein refers to oligosaccharides, disaccharides, monosaccharides, and/or mixtures thereof. The term "saccharide" also includes carbohydrates including starches, dextrans, glycogens, cellulose, pentosans, as well as sugars.

"Undissolved solids" as used herein refers to non-fermentable portions of feedstock which are not dissolved in the liquid or aqueous phase, for example, germ, fiber, and gluten. The non-fermentable portions of feedstock include the portion of feedstock that remains as solids and can absorb liquid from the fermentation broth.

"Product alcohol" as used herein refers to any alcohol that may be produced by a microorganism in a fermentation process that utilizes biomass as a fermentable carbon source. Product alcohols include, but are not limited to, $C_1$ to $C_8$ alkyl alcohols. In some embodiments, the product alcohols may be $C_2$ to $C_8$ alkyl alcohols. In some embodiments, the product alcohols may be $C_2$ to $C_5$ alkyl alcohols. It will be appreciated that $C_1$ to $C_8$ alkyl alcohols include, but are not limited to, methanol, ethanol, propanol, butanol, pentanol, and isomers thereof. Likewise, $C_2$ to $C_8$ alkyl alcohols include, but are not limited to, ethanol, propanol, butanol, pentanol, and isomers thereof "Alcohol" is also used herein with reference to a product alcohol.

"Butanol" as used herein refers to butanol isomers: 1-butanol (1-BuOH), 2-butanol (2-BuOH), tertiary-butanol (tert-BuOH), and/or isobutanol (iBuOH, i-BuOH, or I-BUOH), either individually or as mixtures thereof. Isobutanol as used herein may also be referred to as 2-methyl-1-propanol, isobutyl alcohol, or 2-methylpropan-1-ol.

"Propanol" as used herein refers to the propanol isomers: isopropanol or 1-propanol.

"Pentanol" as used herein refers to the pentanol isomers: 1-pentanol, 3-methyl-1-butanol, 2-methyl-1-butanol, 2,2-dimethyl-1-propanol, 3-pentanol, 2-pentanol, 3-methyl-2-butanol, or 2-methyl-2-butanol.

"Dried Distillers' Grains with Solubles" (DDGS) as used herein refer to a co-product or by-product from a fermentation of a feedstock or biomass (e.g., fermentation of grain or grain mixture that produces a product alcohol). In some embodiments, DDGS may also refer to an animal feed produced from a process of making a product alcohol.

"Portion" as used herein with reference to a process stream refers to any fractional part of the stream which retains the composition of the stream, including the entire stream, as well as any component or components of the stream, including all components of the stream.

The present invention provides processes and systems for producing fermentative products such as product alcohols using fermentation processes. As an example, feedstock may be liquefied to create a feedstock slurry which includes soluble sugars, oil, and undissolved solids. If the feedstock slurry is fed directly to a fermentor, the undissolved solids and/or oil may interfere with efficient recovery of product alcohol. For example, if liquid-liquid extraction is utilized to extract product alcohol from fermentation broth, the presence of undissolved solids may cause system inefficiencies including, but not limited to, decreasing the mass transfer rate of the product alcohol to the extractant by interfering with the contact between the extractant and the fermentation broth; creating an emulsion in the fermentor and thereby interfering with phase separation of the extractant and the fermentation broth; slowing disengagement of the extractant from the fermentation broth; reducing the efficiency of recovering and recycling the extractant because at least a portion of the extractant and product alcohol becomes "trapped" in the undissolved solids; shortening the life cycle of the extractant by contamination with oil; and lowering fermentor volume efficiency because solids are taking up volume in the fermentor. These effects can result in higher capital and operating costs. In addition, extractant "trapped" in undissolved solids used to generate Distillers' Dried Grains with Solubles (DDGS), may detract from the value of DDGS and qualification for sale as animal feed. Therefore, in order to avoid and/or minimize these problems, at least a portion of the undissolved solids may be removed from the feedstock slurry prior to the addition of the feedstock slurry to the fermentor. Extraction activity and the efficiency of product alcohol production and/or recovery can be increased when extraction is performed on fermentation broth containing an aqueous solution where undissolved solids have been removed relative to extraction performed on fermentation broth containing an aqueous solution where undissolved solids have not been removed.

The processes and systems of the present invention will be described with reference to the Figures. In some embodiments, as shown, for example, in FIG. 1, the system includes liquefaction 10 configured to liquefy a feedstock to create a feedstock slurry.

For example, feedstock 12 may be introduced to liquefaction 10. Feedstock 12 may be any suitable biomass material that contains a fermentable carbon source such as starch. Biomass may include, but is not limited to, barley, oat, rye, sorghum, wheat, triticale, spelt, millet, cane, corn, or combinations thereof.

The process of liquefying feedstock 12 involves hydrolysis of feedstock 12 generating water-soluble sugars. Any known liquefying processes utilized by the industry may be used including, but not limited to, an acid process, an enzyme process, or an acid-enzyme process. Such processes may be used alone or in combination. In some embodiments, the enzyme process may be utilized and an appropriate enzyme 14, for example, alpha-amylase, is introduced to liquefaction 10. Examples of alpha-amylases that may be used in the processes and systems of the present invention are described in U.S. Pat. No. 7,541,026; U.S. Patent Application Publication No. 2009/0209026; U.S. Patent Application Publication No. 2009/0238923; U.S. Patent Application Publication No. 2009/0252828; U.S. Patent Application Publication No. 2009/0314286; U.S. Patent Application Publication No. 2010/02278970; U.S. Patent Application Publication No. 2010/0048446; U.S. Patent Application Publication No. 2010/0021587, the entire contents of each are herein incorporated by reference.

The process of liquefying feedstock 12 creates feedstock slurry 16 that includes a fermentable carbon source (e.g., sugar), oil, and undissolved solids. The undissolved solids are non-fermentable portions of feedstock 12. In some embodiments, feedstock 12 may be corn such as dry milled, unfractionated corn kernels, and the undissolved solids may include germ, fiber, and gluten. In some embodiments, feedstock 12 is corn or corn kernels and feedstock slurry 16 is a corn mash. Feedstock slurry 16 may be discharged from liquefaction 10 and conducted to separation 20.

Separation 20 may be configured to remove undissolved solids from feedstock slurry 16. Separation 20 may also be configured to remove oil, or to remove both oil and undissolved solids. Separation 20 may be any device capable of separating solids and liquids. For example, separation 20 may be any conventional centrifuge utilized in the industry including, for example, a decanter bowl centrifuge, three-phase centrifuge, disk stack centrifuge, filtering centrifuge, or decanter centrifuge. In some embodiments, separation may be accomplished by filtration, microfiltration, vacuum filtration, beltfilter, pressure filtration, membrane filtration, crossflow filtration, drum filter, filtration using a screen, screen separation, rotary screen, grates or grating, porous grating, flotation, hydroclone, filter press, screwpress, gravity settler, vortex separator, or any method or separation device that may be used to separate solids and liquids. In some embodiments, separation may be accomplished using two or more separation means such as decanter bowl centrifugation, three-phase centrifugation, disk stack centrifugation, filtering centrifugation, decanter centrifugation, filtration, microfiltration, vacuum filtration, beltfilter, pressure filtration, membrane filtration, crossflow filtration, drum filter, filtration using a screen, screen separation, rotary screen, grating, porous grating, flotation, hydrocyclone, filter press, screwpress, gravity settler, vortex separator, or combination thereof.

Feedstock slurry 16, conducted to separation 20, may be separated into a first liquid phase or aqueous solution 22 containing a fermentable sugar, a second liquid phase containing oil 26, and a solid phase or wet cake 24 containing undissolved solids. As an example, feedstock slurry 16 may be separated using a three-phase centrifuge. A three-phase centrifuge allows for three-phase separation yielding two liquid phases (e.g., aqueous stream and oil stream) and a solid phase (e.g., solids or wet cake) (see, e.g., Flottweg Tricanter®, Flottweg AG, Vilsibiburg, Germany). The two liquid phases may be separated and decanted, for example, from a bowl via two discharge systems to prevent cross-contamination and the solids phase may be removed via a separate discharge system.

In some embodiments using corn as feedstock 12, a three-phase centrifuge may be used to remove solids and corn oil simultaneously from feedstock slurry 16 (e.g., liquefied corn mash). The solids are the undissolved solids remaining after the starch is hydrolyzed to soluble oligosaccharides during liquefaction, and the corn oil is oil that is released from the germ during grinding and/or liquefaction. In some embodiments, the three-phase centrifuge may have one feed stream and three outlet streams. The feed stream may consist of liquefied corn mash produced during liquefaction. The mash may consist of an aqueous solution of liquefied starch (e.g., oligosaccharides); undissolved solids which consist of insoluble, non-starch components from the corn; and corn oil which consists of glycerides and free fatty acids. The three outlet streams from the three-phase centrifuge may be a wet cake (i.e., wet cake 24) which contains most of the undissolved solids from the mash; a heavy centrate stream which contains most of the liquefied starch from the mash; and a light centrate stream which contains most of the corn oil from the mash. In some embodiments, the light centrate stream (i.e., oil 26) may be conducted to a storage tank or any vessel that is suitable for oil storage. In some embodiments, the oil may be sold as a co-product, converted to another co-product, or used in processing such as the case in converting corn oil to corn oil fatty acids.

In some embodiments, when oil 26 is removed via separation 20 from feedstock slurry 16, the fermentation broth in fermentation 30 includes a reduced amount of oil. The amount of oil in the feedstock slurry can depend on the biomass. For example, some corn may contain about 3-6% corn oil (dry corn basis). In some embodiments of the processes and systems described herein, feedstock slurry may comprise at least 0.5 wt %, at least 1 wt %, at least 2 wt %, at least 3 wt %, at least 4 wt %, or at least 5 wt % oil.

The heavy centrate stream (i.e., aqueous solution 22) may be added to fermentation 30. Aqueous solution 22 may include sugar, for example, in the form of oligosaccharides, and water. Aqueous solution 22 may comprise at least about 5% by weight oligosaccharides, at least about 10% by weight oligosaccharides, at least about 15% by weight oligosaccharides, at least about 20% by weight of oligosaccharides, at least about 25% by weight oligosaccharides, or at least about 30% by weight of oligosaccharides. Aqueous solution 22 may have a viscosity of less than about 20 centipoise. Aqueous solution 22 may comprise less than about 20 g/L of monomeric glucose, less than about 15 g/L of monomeric glucose, less than about 10 g/L of monomeric glucose, or less than about 5 g/L of monomeric glucose. Suitable methodology to determine the amount of monomeric glucose is well known in the art such as high performance liquid chromatography (HPLC).

In some embodiments, aqueous solution 22 formed from feedstock slurry 16 includes no more than about 50% by weight of the undissolved solids present in the feedstock slurry, no more than about 45% by weight of the undissolved solids present in the feedstock slurry, no more than about 40% by weight of the undissolved solids present in the feedstock slurry, no more than about 35% by weight of the undissolved solids present in the feedstock slurry, no more than about 30% by weight of the undissolved solids present in the feedstock slurry, no more than about 25% by weight of the undissolved solids present in the feedstock slurry, no more than about 20% by weight of the undissolved solids present in the feedstock slurry, no more than about 15% by weight of the undissolved solids present in the feedstock slurry, no more than about 10% by weight of the undissolved solids present in the feedstock slurry, no more than about 5% by weight of the undissolved solids present in the feedstock slurry, no more than about 4% by weight of the undissolved solids present in the feedstock slurry, no more than about 3% by weight of the undissolved solids present in the feedstock slurry, no more than about 2% by weight of the undissolved solids present in the feedstock slurry, or no more than about 1% by weight of the undissolved solids present in the feedstock slurry.

In some embodiments, the separation step may remove at least about 80%, at least about 85%, at least about 90%, at least about 95%, at least about 96%, at least about 97%, at least about 98%, or at least about 99% of the suspended solids from the mash. In some embodiments, aqueous solution 22 may comprise at least about 0.5%, at least about 1%, at least about 1.5%, or at least about 2% suspended solids.

Wet cake 24 may be discharged from separation 20. Wet cake 24 may also include a portion of sugar and water. Wet cake 24 may be washed with additional water using separation 20. Alternatively, wet cake 24 may be washed with additional water using additional separation devices. In some embodiments, wet cake 24 may be washed with process recycle water, such as evaporator condensate and/or backset. Washing wet cake 24 will recover the sugar or soluble starch present in the wet cake, and the recovered sugar and water may be recycled to liquefaction 10. After washing, wet cake 24 may be further processed to form DDGS using any suitable known process. The formation of DDGS from wet cake 24 has several benefits. For example, since the undissolved solids are not added to the fermentor, the undissolved solids do not contact the microorganisms present in the fermentor, the undissolved solids are not subjected to the conditions of the fermentor, and product alcohol or other components such as extractant are not trapped in the undissolved solids. These effects provide benefits to subsequent processing and use of DDGS, for example, as animal feed because the DDGS would not contain microorganism or other components (e.g., product alcohol, extractant) of the fermentation broth.

In some embodiments, wet cake 24 formed from feedstock slurry 16 includes at least about 50% by weight of the undissolved solids present in the feedstock slurry, at least about 55% by weight of the undissolved solids present in the feedstock slurry, at least about 60% by weight of the undissolved solids present in the feedstock slurry, at least about 65% by weight of the undissolved solids present in the feedstock slurry, at least about 70% by weight of the undissolved solids present in the feedstock slurry, at least about 75% by weight of the undissolved solids present in the feedstock slurry, at least about 80% by weight of the undissolved solids present in the feedstock slurry, at least about 85% by weight of the undissolved solids present in the feedstock slurry, at least about 90% by weight of the undissolved solids present in the feedstock slurry, at least about 95% by weight of the undissolved solids present in the feedstock slurry, at least about 96% by weight of the undissolved solids present in the feedstock slurry, at least about 97% by weight of the undissolved solids present in the feedstock slurry, at least about 98% by weight of the undissolved solids present in the feedstock slurry, or at least about 99% by weight of the undissolved solids present in the feedstock slurry.

In some embodiments, the volume of the fermentor taken up by undissolved solids may be decreased by removal of these solids. Thus, the effective volume of the fermentor available for the fermentation can be increased. In some embodiments, the volume of the fermentor available for the fermentation may be increased by at least about 5%, at least about 10%, or at least about 15%.

Fermentation 30 configured to ferment aqueous solution 22 to produce a product alcohol has an inlet for receiving aqueous solution 22. Fermentation 30 may include fermentation broth and microorganism 32. In some embodiments, microorganism 32 metabolizes the fermentable carbon source in aqueous solution 22 and produces product alcohol. Stream 35 or a portion thereof comprising product alcohol and fermentation broth may be discharged from fermentation 30 and further processed for recovery of product alcohol and the fermentation broth may be recycled to fermentation 30.

Stream 35 or a portion thereof may include no more than about 50% by weight of the undissolved solids present in the feedstock slurry, no more than about 45% by weight of the undissolved solids present in the feedstock slurry, no more than about 40% by weight of the undissolved solids present in the feedstock slurry, no more than about 35% by weight of the undissolved solids present in the feedstock slurry, no more than about 30% by weight of the undissolved solids present in the feedstock slurry, no more than about 25% by weight of the undissolved solids present in the feedstock slurry, no more than about 20% by weight of the undissolved solids present in the feedstock slurry, no more than about 15% by weight of the undissolved solids present in the feedstock slurry, no more than about 10% by weight of the undissolved solids present in the feedstock slurry, no more than about 5% by weight of the undissolved solids present in the feedstock slurry, no more than about 4% by weight of the undissolved solids present in the feedstock slurry, no more than about 3% by weight of the undissolved solids present in the feedstock slurry, no more than about 2% by weight of the undissolved solids present in the feedstock slurry, or no more than about 1% by weight of the undissolved solids present in the feedstock slurry.

In some embodiments, feedstock slurry 16 or aqueous solution 22 may be subjected to saccharification. Any known saccharification process utilized by the industry may be used including, but not limited to, an acid process, an acid-enzyme process, or an enzyme process. In some embodiments, an enzyme such as glucoamylase may be introduced to hydrolyze sugars (e.g., oligosaccharides) in feedstock slurry 16 or aqueous solution 22 to form monosaccharides. Examples of glucoamylases that may be used in the processes and systems of the present invention are described in U.S. Pat. No. 7,413,887; U.S. Pat. No. 7,723,079; U.S. Patent Application Publication No. 2009/0275080; U.S. Patent Application Publication No. 2010/0267114; U.S. Patent Application Publication No. 2011/0014681; U.S. Patent Application Publication No. 2011/0020899, the entire contents of each are herein incorporated by reference. In some embodiments, enzymes such as glucoamylases may be added to liquefaction. The addition of glucoamylases to liquefaction may reduce the viscosity of the feedstock slurry or liquefied mash.

In some embodiments, the processes and systems of the present invention may include a mill configured to process feedstock. In some embodiments, the mill may be any suitable mill utilized in the industry. In some embodiments, the feedstock may be fractionated or wet milled, or the feedstock may be unfractionated or dry milled. Wet milling is a multi-step process that separates biomass into several components such as germ, pericarp fiber, starch, and gluten in order to capture value from each co-product separately. Using corn as a feedstock, this process produces several co-products: starch, gluten feed, gluten meal, and corn oil.

These streams may be recombined and processed to produce customized products for the feed industry. For example, starch may be further processed via fermentation to produce an alcohol or may be utilized by the food, paper, or textile industries. Gluten meal and gluten feed stream which both contain protein, fat, and fiber, may be used in feeds for dairy and beef cattle, poultry, swine, livestock, equine, aquaculture, and domestic pets.

Dry milling may also be utilized for feedstock processing. Feedstock may be milled, for example, using a hammermill to generate a meal that may then be mixed with water to form feedstock slurry. The feedstock slurry may be subjected to liquefaction and further processed as described herein.

Following fermentation, the fermentation broth may be conducted to distillation for recovery of product alcohol. If undissolved solids have not been removed, the bottoms stream of the distillation column, whole stillage, contains unfermented solids (e.g., distiller's grain solids), dissolved materials, and water. For example, whole stillage may be separated into solids (e.g., wet cake) and thin stillage. Separation may be accomplished by a number of means including, but not limited to, centrifugation, filtration, screen separation, hydrocyclone, or any other means or separation device for separating liquids from solids. Thin stillage may be conducted to evaporation forming condensed distillers solubles (CDS) or syrup. The wet cake may be combined with syrup and then dried to form DDGS which may be used in animal feeds for dairy and beef cattle, poultry, swine, livestock, equine, aquaculture, and domestic pets.

Figure 2:
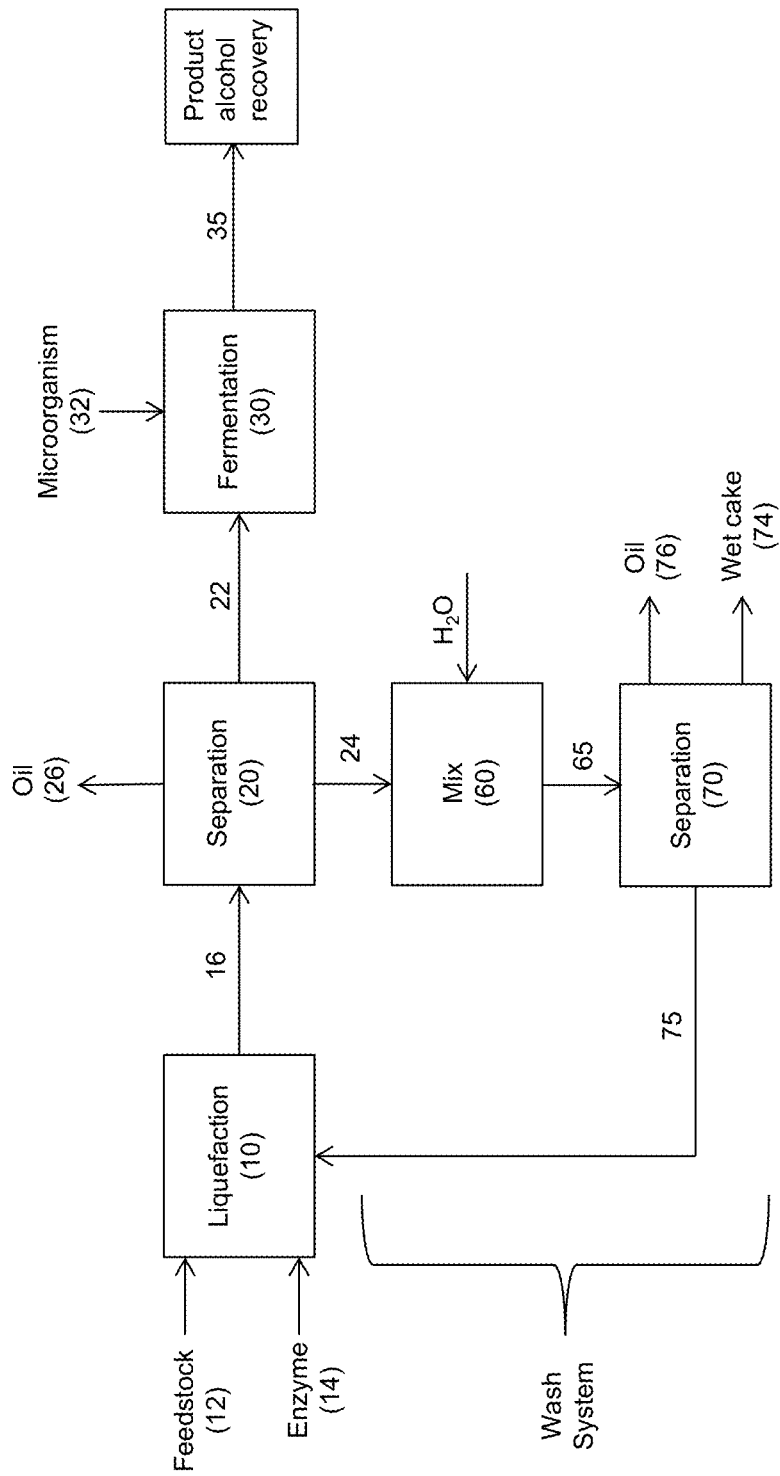
FIG. 2 schematically illustrates another exemplary alternative process and system of the present invention, in which the separation unit discharges an oil stream and wet cake is subjected to wash cycles.

In some embodiments, the process and system of FIG. 1 may be modified to include one or more wash systems for processing of wet cake 24 as shown in FIG. 2. Other processes illustrated in FIG. 2 including liquefaction 10 and fermentation 30 are similar to FIG. 1, and are not described in detail again.

As illustrated in FIG. 2, oil and undissolved solids may be removed at various points during the processes described herein. Feedstock slurry 16 may be separated into a first liquid phase or aqueous solution 22, a second liquid phase comprising oil 26, and a solid phase or wet cake 24. Wet cake 24 may be further processed to recover fermentable sugars and oil remaining in the solid phase. Wet cake 24 may be conducted to mix 60 and combined with water or other solvents forming wet cake mixture 65. In some embodiments, water may be backset, cook water, process water, lutter water, water collected from evaporation, or any water source available in the fermentation processing facility, or any combination thereof. In some embodiments, solvents such as hexane, isobutanol, isohexane, ethanol, petroleum distillates such as petroleum ether, or mixtures thereof may be used to recover oil from wet cake. Wet cake mixture 65 may be conducted to separation 70 producing wash centrate 75 comprising fermentable sugars, oil stream 76, and wet cake 74. Wash centrate 75 may be recycled to liquefaction 10.

In some embodiments, separation 70 may be any separation device capable of separating solids and liquids including, for example, decanter bowl centrifugation, three-phase centrifugation, disk stack centrifugation, filtering centrifugation, decanter centrifugation, filtration, microfiltration, vacuum filtration, beltfilter, pressure filtration, membrane filtration, crossflow filtration, drum filter, filtration using a screen, screen separation, rotary screen, grating, porous grating, flotation, hydrocyclone, filter press, screwpress, gravity settler, vortex separator, or combination thereof.

In some embodiments, wet cake may be subjected to one or more wash cycles or wash systems. For example, wet cake 74 may be further processed by conducting wet cake 74 to a second wash system. In some embodiments, wet cake 74 may be conducted to a second mix 60' forming wet cake mixture 65'. Wet cake mixture 65' may be conducted to a second separation 70' producing wash centrate 75', oil stream 76', and wet cake 74'. Wash centrate 75' may be recycled to liquefaction 10, and wet cake 74' may be combined with wet cake 74 for further processing. In some embodiments, wash centrate 75' may be combined with wash centrate 75 and the combined wash centrates may be recycled to liquefaction 10. Oil stream 76' and oil 26 may be combined and further processed for the manufacture of various consumer products.

In some embodiments, separation 70' may be any separation device capable of separating solids and liquids including, for example, decanter bowl centrifugation, three-phase centrifugation, disk stack centrifugation, filtering centrifugation, decanter centrifugation, filtration, microfiltration, vacuum filtration, beltfilter, pressure filtration, membrane filtration, crossflow filtration, drum filter, filtration using a screen, screen separation, rotary screen, grating, porous grating, flotation, hydrocyclone, filter press, screwpress, gravity settler, vortex separator, or combination thereof.

In some embodiments, the wet cake may comprise at least about 5%, at least about 10%, at least about 15%, at least about 20%, at least about 25%, at least about 30%, at least about 35%, or more fermentable sugars from the feedstock slurry. In some embodiments, the wet cake may be subjected to one, two, three, four, five, six, seven, eight, nine, ten or more wash cycles or wash systems. In some embodiments, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more fermentable sugars may be recovered from the washed wet cake.

In some embodiments, the wet cake may be combined with solubles and then dried to form DDGS using any suitable known process. Oil such as corn oil contains triglycerides, fatty acids, diglycerides, monoglycerides, and phospholipids and provides a source of metabolizable energy for animals. In some embodiments, oil may be added to the wet cake and further processed to form DDGS and ultimately used to generate a high fat content animal feed.

In some embodiments, oil may be converted to an extractant for use in the recovery of product alcohol. Methods for deriving extractants from biomass are described in U.S. Patent Application Publication No. 2011/0312043, U.S. Patent Application Publication No. 2011/0312044, and PCT International Publication No. WO 2011/159998; the entire contents of each are herein incorporated by reference. For example, oil may be hydrolyzed by a catalyst such as an esterase converting the triglycerides in the oil to fatty acids such as carboxylic acids. These fatty acids may be used as extractant for the recovery of the product alcohol.

Removal of the oil component of the feedstock is advantageous to product alcohol production because oil present in the fermentor can break down into fatty acids and glycerin. The glycerin can accumulate in the water and reduce the amount of water that is available for recycling throughout the system. Thus, removal of the oil component of the feedstock increases the efficiency of the product alcohol production by increasing the amount of water that can be recycled through the system. Additional benefits for oil removal from feedstock slurry include increased oil yield, improved oil quality (e.g., cleaner, higher-quality oil), reduced system deposition, and reduced downtime.

Figure 3:
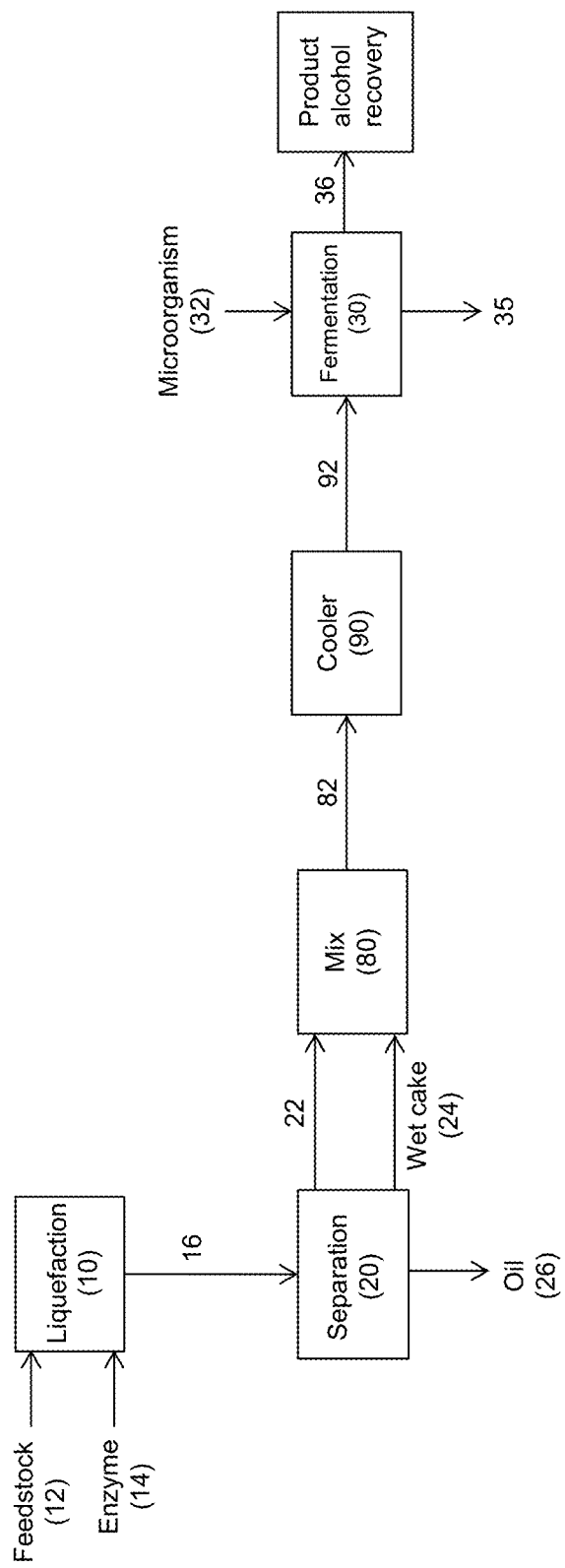
FIG. 3 schematically illustrates another exemplary alternative process and system of the present invention, in which the aqueous solution and wet cake are combined and conducted to fermentation.

In some embodiments, the process and system of FIG. 1 may be modified to include oil removal as shown in FIG. 3. Other processes illustrated in FIG. 3 including liquefaction 10 and fermentation 30 are similar to FIG. 1, and are not described in detail again.

As illustrated in FIG. 3, aqueous solution 22 and wet cake 24 may be combined, cooled, and conducted to fermentation 30. Feedstock slurry 16 may be separated, for example, using a three-phase centrifuge, into a first liquid phase or aqueous solution 22, a second liquid phase comprising oil 26, and a solid phase or wet cake 24. In some embodiments, oil 26 may be conducted to a storage tank or any vessel that is suitable for oil storage. Aqueous solution 22 and wet cake 24 may be conducted to mix 80 and re-slurried forming aqueous solution/wet cake mixture 82. Mixture 82 may be conducted to cooler 90 producing cooled mixture 92 which may be conducted to fermentation 30. In some embodiments, when oil 26 is removed via separation 20 from feedstock slurry 16, mixtures 82 and 92 include a reduced amount of corn oil.

Figure 4:
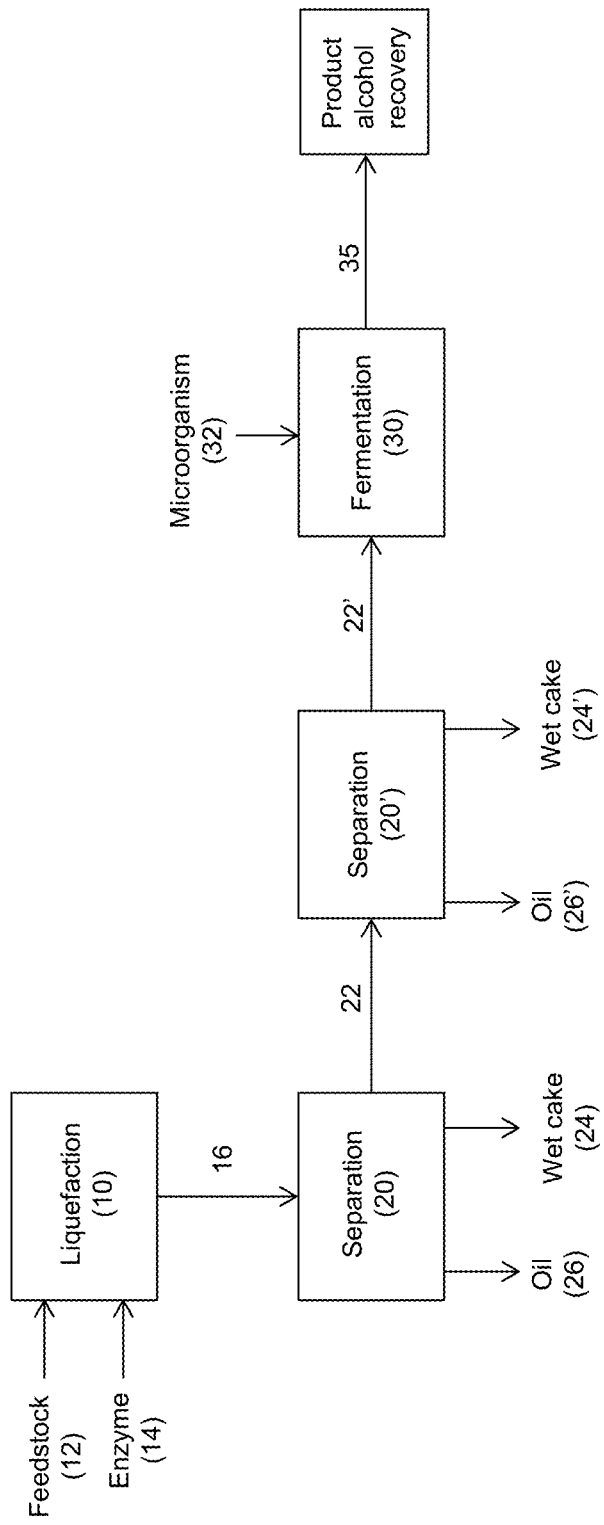
FIG. 4 schematically illustrates another exemplary alternative process and system of the present invention, in which two separation units are utilized in series to remove the undissolved solids.

In some embodiments, as shown, for example, in FIG. 4, the processes and systems of the present invention may include a series of two or more separation devices. FIG. 4 is similar to FIG. 1, except for the addition of a second separation system 20' and therefore, will not be described in detail again.

Aqueous solution 22 discharged from separation 20 may be conducted to separation 20'. Separation 20' may be identical to separation 20 and may operate in the same manner. Separation 20' may remove undissolved solids and oil not separated from aqueous solution 22 to generate (i) an aqueous solution 22' similar to aqueous solution 22, but containing reduced amounts of undissolved solids and oil in comparison to aqueous solution 22, and (ii) a wet cake 24' similar to wet cake 24, and (iii) an oil stream 26' similar to oil 26. Aqueous solution 22' may then be introduced to fermentation 30. In some embodiments, there can be one or more additional separation devices after separation 20'.

In some embodiments, separation 20' may be any separation device capable of separating solids and liquids including, for example, decanter bowl centrifuge, three-phase centrifuge, disk stack centrifuge, filtering centrifuge, or decanter centrifuge. In some embodiments, separation may be accomplished by filtration, microfiltration, vacuum filtration, beltfilter, pressure filtration, membrane filtration, crossflow filtration, drum filter, filtration using a screen, screen separation, rotary screen, grates or grating, porous grating, flotation, hydroclone, filter press, screwpress, gravity settler, vortex separator, or combination thereof.

Figure 5:
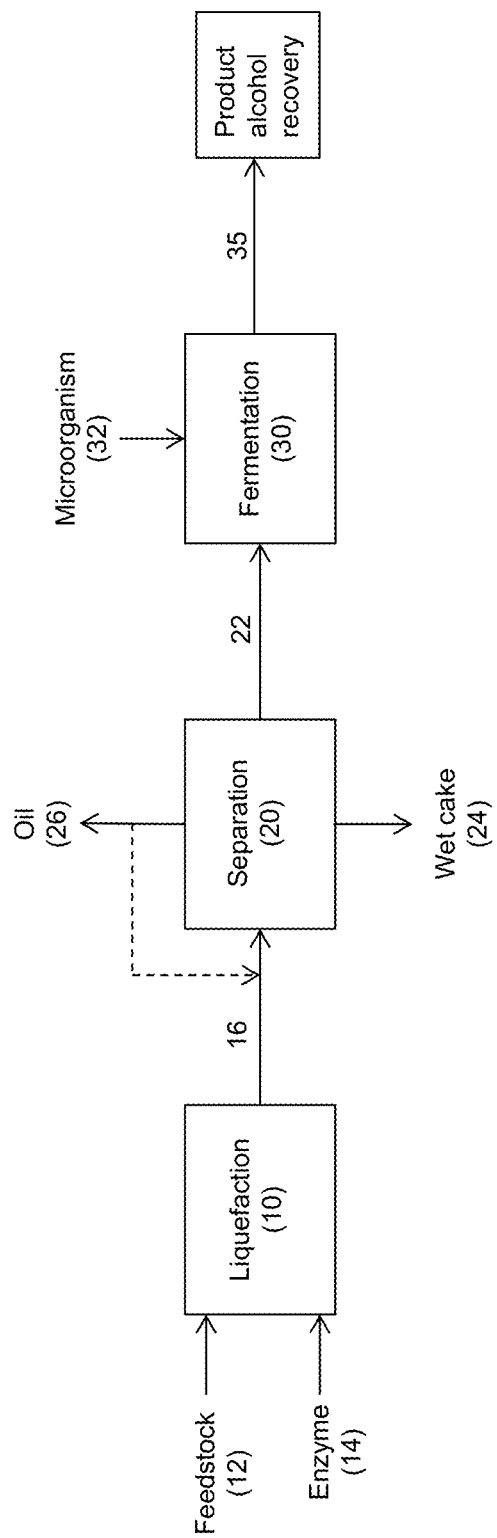
FIG. 5 schematically illustrates another exemplary alternative process and system of the present invention, in which oil is returned to the separation unit.

In another embodiment, as shown, for example, in FIG. 5, the processes and systems of the present invention may include an oil recycle stream. FIG. 5 is similar to FIG. 1, except for the addition of the oil recycle stream and therefore will not be described in detail again.

Following separation 20, oil 26 or a portion thereof may be returned (dashed line) to separation 20. In some embodiments, oil 26 may be added to feedstock slurry 16. By increasing the concentration of oil in the feedstock slurry, overall oil recovery may improve. That is, the rate of oil removal is a function of the concentration of oil in the incoming feed and therefore, optimizing the oil concentration in the feed can maximize oil recovery.

Removal of both undissolved solids and oil may provide a number of advantages to the overall fermentation process. For example, nutrients in the fermentation broth may be soluble in oil or may be trapped in the undissolved solids. Removing oil and undissolved solids can minimize the loss of nutrients. The presence of oil and undissolved solids may also have an impact of the scalability of the processes and methods described herein. For example, if liquid-liquid extraction is used to recover product alcohol, the presence of oil in the fermentation process may have an effect on the partition coefficient of the extractant over the course of multiple fermentations. Removing oil from the feedstock or feedstock slurry can reduce the variability of the partition coefficient of the extractant over the course of multiple fermentations, and therefore improve the scalability of the processes and methods described herein. In addition, removing solids from the feedstock slurry may also have an effect on scalability. Reduced solids may enhance the rate of mass transfer of product alcohol. Solid particles may coat the surface of the extractant droplets effectively reducing the area for mass transfer to occur. Solid particles may also inhibit phase separation by increasing viscosity and the tendency for emulsification. Therefore, removing solids and/or oil may improve the scalability of the unit operations of processes and methods described herein. For example, removing solids and/or oil may improve the unit operations such as, but not limited to, extractor performance, distillation column performance, heat exchanger performance, and/or evaporator performance.

The absence or minimization of the undissolved solids exiting fermentation 30 via stream 35 has several benefits. For example, the need for units and operations in the downstream processing may be eliminated, for example, a beer column or distillation column, thereby resulting in an increased efficiency for product alcohol production. Also, some or all of the centrifuges used to process whole stillage may be eliminated as a result of less undissolved solids in the fermentation broth exiting the fermentor.

For the processes and systems described herein, separation of feedstock slurry may be modified by adjusting various control parameters or control settings of the processes and systems. As an example, separation settings may be adjusted to improve separation of oil and undissolved solids from feedstock slurry. In some embodiments where a three-phase centrifuge is used, centrifuge settings such as differential speed, bowl speed, flow rate, and impeller position may be adjusted to improve separation and recovery of oil and undissolved solids. Additional parameters that may be modified to improve separation include, but are not limited to, residence time, scroll pitch, and discharge volume. For example, by adjusting residence time, the moisture content of the wet cake may be increased or decreased.

In another embodiment of the processes and systems described herein, a gating element such as a weir or dip weir may be used in conjugation with a centrifuge to improve separation and recovery of oil. Oil separation and recovery (or light liquid phase separation and recovery) may be enhanced when a dip weir feature is installed on the scroll conveyor of a three-phase centrifuge, near the conical transition zone of the conveyor. In some instances, it appears that a greater than two volume percent (2 vol %) light phase in the feed stream is required in order to successfully isolate the light phase liquid. However, the presence of the dip weir on the scroll conveyor facilitates increased accumulation of oil (or light phase liquid) within the bowl, thus permitting isolation of oil at volume concentrations below about 2 vol % of the starting liquid volume (e.g., feedstock slurry).

Without the dip weir feature, oil (or light phase liquid) on the liquid pool surface is in direct contact with the wet cake solids moving up the conical cake discharge zone of the three-phase centrifuge, thus permitting losses of oil with the wet cake solids. Three-phase centrifuges equipped with the dip weir feature demonstrated that oil may be accumulated by sequestering the oil portion of the liquid pool between the dip weir and a separator disk. This buildup aided in successful recovery of oil removal with centrifuge feed material containing oil concentrations at or below one volume percent (1 vol %).

Dip weir functionality may also enhance solids phase recovery and/or improved centrate (e.g., aqueous solution) quality. For solids phase recovery, the dip weir feature prevents direct contact of liquid pool surface with solids within the conical section drainage zone, thereby yielding centrifuged solids with improved liquid removal. The dip weir also permits build of the liquid pool depth to levels above that of the centrifuge bowl's cake discharge diameter, thus serving to increase residence time of centrate and thus improve solids removal from the centrate liquids. Higher liquid pool depth imparts a higher pressure upon the sedimented solids below, thus further compression of solids which may improve solids dewatering.

In some embodiments of the processes and systems described herein, the weir may improve the separation of the two liquid phases (e.g., aqueous solution and oil). In some embodiments, the weir may have adjustable variable positions. In some embodiments, the levels of the two liquid phases may be adjusted to improve separation. In some embodiments, feedstock slurry may comprise oil in an amount that is less than about two volume percent (2 vol %) of the feedstock slurry. In some embodiments, feedstock slurry may comprise oil in an amount that is less than about 1.5 volume percent (1.5 vol %) of the feedstock slurry. In some embodiments, feedstock slurry may comprise oil in an amount that is less than about one volume percent (1 vol %) of the feedstock slurry.

In some embodiments of the processes and systems described herein, the oil stream may be separated from the feedstock slurry intermittently or in batch mode. During operation of a three-phase centrifuge, the aqueous solution (or heavy liquid phase, heavy centrate stream), the oil phase, and the wet cake may be discharged continuously. During this operation, the quality of the oil phase (e.g., water content and suspended solids concentration) is partly dependent on the thickness of the oil layer in the centrifuge. For example, a thicker oil layer can generate a better quality of oil. The interface between the heavy liquid phase and the oil phase may be adjusted during continuous operation, for example, by adjusting the impeller position. Utilizing an intermittent discharge or batch discharge of the oil phase, the temporary interruption of the oil flow from the centrifuge allows for an accumulation of the oil phase in the centrifuge and therefore, provides for a thicker oil phase layer. When the oil layer reaches a certain thickness, the oil phase may be discharged from the centrifuge. This method provides for a discharged corn oil with improved quality (e.g., decreased water content and suspended solids concentration).

While not wishing to be bound by theory, it is believed that the processes described herein are useful in conjunction with any alcohol producing microorganism, particularly recombinant microorganisms which produce alcohol.

Microorganisms which produce alcohol are known in the art (e.g., Ohta, et al., Appl. Environ. Microbiol. 57:893-900, 1991; Underwood, et al., Appl. Environ. Microbiol. 68:1071-1081, 2002; Shen and Liao, Metab. Eng. 10:312-320, 2008; Hahnai, et al., Appl. Environ. Microbiol. 73:7814-7818, 2007; U.S. Pat. No. 5,514,583; U.S. Pat. No. 5,712,133; PCT Application Publication No. WO 1995/028476; Feldmann, et al., Appl. Microbiol. Biotechnol. 38:354-361, 1992; Zhang, et al., Science 267:240-243, 1995; U.S. Patent Application Publication No. 2007/0031918; U.S. Pat. No. 7,223,575; U.S. Pat. No. 7,741,119; U.S. Patent Application Publication No. 2009/0203099; U.S. Patent Application Publication No. 2009/0246846; and PCT Application Publication No. WO 2010/075241, which are herein incorporated by reference).

In some embodiments, the microorganism may be genetically modified. For example, the metabolic pathways of microorganisms may be genetically modified to produce a product alcohol. These pathways may also be modified to reduce or eliminate undesired metabolites, and thereby improve yield of the product alcohol. The production of butanol by a microorganism is disclosed, for example, in U.S. Patent Application Publication Nos. 2007/0092957; 2007/0259410; 2007/0292927; 2008/0182308; 2008/0274525; 2009/0305363; and 2009/0305370, the entire contents of each are herein incorporated by reference. In some embodiments, microorganisms may comprise a butanol biosynthetic pathway or a biosynthetic pathway for a butanol isomer such as 1-butanol, 2-butanol, or isobutanol. In some embodiments, the microorganism may be bacteria, cyanobacteria, filamentous fungi, or yeasts. Suitable microorganisms capable of producing product alcohol via a biosynthetic pathway include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Zygosaccharomyces, Debaryomyces, Candida, Brettanomyces, Pachysolen, Hansenula, Issatchenkia, Trichosporon, Yamadazyma,* or *Saccharomyces*. In some embodiments, microorganisms may be selected from the group consisting of *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis, Candida sonorensis, Candida methanosorbosa, Kluyveromyces lactis, Kluyveromyces marxianus, Kluyveromyces thermotolerans, Issatchenkia orientalis, Debaryomyces hansenii,* and *Saccharomyces cerevisiae.* In some embodiments, the microorganism may be yeast. In some embodiments, the microorganism may be crabtree-positive yeast selected from *Saccharomyces, Zygosaccharomyces, Schizosaccharomyces, Dekkera, Torulopsis, Brettanomyces,* and some species of *Candida.* Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Saccharomyces uvarum, Saccharomyces castelli, Saccharomyces kluyveri, Zygosaccharomyces rouxii, Zygosaccharomyces bailli,* and *Candida glabrata.*

Further, while various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the exemplary embodiments described herein, but should be defined only in accordance with the claims and their equivalents.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

EXAMPLES

The following nonlimiting examples will further illustrate the invention. It should be understood that, while the following examples involve corn as feedstock, other biomass sources can be used for feedstock without departing from the present invention.

As used herein, the meaning of abbreviations used was as follows: "g" means gram(s), "kg" means kilogram(s), "lbm" means pound mass, "gpm" means gallons per minute, "gal" means gallon(s), "L" means liter(s), "mL" means milliliter(s), "µL" means microliter(s), "mL/L" means milliliter(s) per liter, "mL/min" means milliliter(s) per min, "min" means minute(s), "hr" means hour(s), "µM" means micrometer(s), "mm" means millimeter(s), "nm" means nanometer(s), "w/v" means weight/volume, "wt %" means weight percent, "dcw" means dry cell weight, "rpm" means revolutions per minute, "° C." means degree(s) Celsius, "slpm" means standard liter(s) per minute, "ppm" means part per million.

Example 1

Separation of Corn Oil and Undissolved Solids from Corn Mash

Approximately 1000 g of liquefied corn mash was prepared in a 1 L glass, jacketed resin kettle. The kettle was set up with mechanical agitation, temperature control, and pH control. The following protocol was used: mixed ground corn with tap water (26 wt % corn on a dry basis), heated the slurry to 55° C. while agitating, adjusted pH to 5.8 with either NaOH or $H_2SO_4$, added alpha-amylase (0.02 wt % on a dry corn basis), continued heating to 85° C., adjusted pH to 5.8, held at 85° C. for 2 hr while maintaining pH at 5.8, cool to 25° C. The corn was ground in a hammer-mill using a 1 mm screen. The moisture content of the ground corn was about 11.7 wt %, and the starch content of the ground corn was about 71.4 wt % on a dry corn basis. The alpha-amylase enzyme was Liquozyme® SC DS (Novozymes, Franklinton, N.C.). The total amounts of the ingredients used were: 294.5 g ground corn (11.7% moisture), 705.5 g tap water, and 0.059 g Liquozyme® SC DS. Water (4.3 g) was added to dilute the enzyme, and a total of 2.3 g of 20% NaOH solution was added to control pH. About 952 g of mash was recovered.

Corn oil and undissolved solids were separated from mash using a three-phase centrifuge (Flottweg Tricanter® Z23-4 bowl diameter, 230 mm, length to diameter ratio 4:1) under these conditions:
Differential Speed: 10 rpm
Feed Rate: 3 gpm
Phase Separator Disk: 138 mm
Impeller Setting: 144 mm The corn oil separate had 81% triglycerides, 6% free fatty acids, 4% diglycerides, and 5% total phospholipids and monoglycerides as determined by thin layer chromatography.

The solids separated from mash had a moisture content of 58% as determined by weight loss upon drying and had 1.2% triglycerides and 0.27% free fatty acids.

The composition of solids separated from whole stillage, oil extracted between evaporator stages, by-product extractant, and Condensed Distillers Solubles (CDS) in Table 1 were calculated assuming the composition of whole stillage shown in Table 2 and the assumptions in Table 3 (separation at three-phase centrifuge). The values of Table 2 were obtained from an Aspen Plus® model (Aspen Technology, Inc., Burlington, Mass.). This model assumes that corn oil is not extracted from mash. It is estimated that the protein content on a dry basis of cells, dissolved solids, and suspended solids is about 50%, about 22%, and about 35.5%, respectively. The composition of by-product extractant is estimated to be about 70.7% free fatty acid (FFA) and about 29.3% fatty acid isobutyl ester (FABE) on a dry basis.

TABLE 1

| Stream | Protein | Triglyceride | FFA | FABE |
|---|---|---|---|---|
| Whole stillage wet cake | 40% | trace | 0.5% | 2.2% |
| Oil at evaporator | 0% | 0.08% | 16.1% | 73.8% |
| CDS | 22% | trace % | 0.37% | 1.71% |

TABLE 2

| Component | Mass % |
|---|---|
| Water | 57.386% |
| Cells | 0.502% |
| Fatty acids | 6.737% |
| Isobutyl esters of fatty acids | 30.817% |
| Triglyceride | 0.035% |
| Suspended solids | 0.416% |
| Dissolved solids | 4.107% |

TABLE 3

|  | Hydrolyzer feed | Thin stillage | Solids |
|---|---|---|---|
| Organics | 99.175% | 0.75% | 0.08% |
| Water and dissolved solids | 1% | 96% | 3% |
| Suspended solids and cells | 1% | 2% | 97% |

Example 2

Removal of Corn Oil from Liquefied Corn Mash

This example describes the use of a three-phase centrifuge to remove corn oil from liquefied corn mash. Liquefied corn mash was generated using a standard continuous liquefaction process as used, for example, in a dry-grind corn-to-ethanol process. The ground corn contained 4.16 wt % corn oil (dry corn basis) and had a moisture content of 14.7 wt %. Ground corn and water were fed to a slurry tank at 10.2 lbm/min and 17.0 lbm/min, respectively, to give a dry corn loading of 32 wt %. Alpha-amylase was fed to the slurry tank at a rate that corresponded to an enzyme loading of about 0.025 wt % on a dry corn basis. The slurry and liquefaction tanks were both run at 85° C. and pH of 5.8. The total residence time at 85° C. was about 2 hr. Mash was produced at a rate of about 3 gpm and contained about 1.3 wt % corn oil on a wet basis. A portion of this oil existed as free oil and a portion was in the undissolved solids. This corresponds to a total corn oil content of the mash to be about 2.0 lbm of corn oil/bushel of corn. The total solids (TS) in the mash was 32 wt % and the total suspended solids (TSS) was 7.7 wt %.

The liquefied corn mash was fed to a three-phase centrifuge (Model Z23-4/441, Flottweg Tricanter®, Flottweg AG, Vilsibiburg, Germany) at a rate of about 3 gpm. The feed temperature was about 80° C. The mash was separated into three streams: (1) corn oil, (2) aqueous solution of oligosaccharides (liquefied starch), and (3) wet cake. The operating conditions of the three-phase centrifuge were as follows:
   Bowl Speed: 5000 rpm
   G-force: 3200 g
   Differential speed: 10 rpm
   Impeller setting: approximately 145 mm
   Phase separator disk: approximately 138 mm Table 4 summarizes data (flow rate, density, solids content, and corn oil content) measured for the feed stream and the three exit streams from the three-phase centrifuge.

TABLE 4

|  | Feed Mash | Aqueous Centrate | Wet Cake | Corn Oil |
|---|---|---|---|---|
| Flow Rate, lbm/min: | 27.2 | 19.5 | 7.6 | 0.14 |
| Density, g/ml: | 1.1008 | ~1.09 |  | 0.875 |
| Total Solids, wt %: | 32.0 | 28.7 | 39.1 | ~0 |
| Total Suspended Solids, wt %: | 7.7 | 4.3 | 16.6 | ~0 |
| Corn Oil Content (wet basis), wt %: | 1.3 | 0.38 | 1.95 | 99.4 * |
| Corn Oil Content, lbm/bushel: | 2.0 | 0.4 | 0.8 | 0.8 |
| % of Corn Oil in feed: | NA | 20 | 41 | 39 |

* Balance is water

The corn oil removed from the mash by the three-phase centrifuge accounted for about 39% of the total corn oil in the mash feed. The corn oil removal rate was equal to about 0.8 lbm/bushel of corn. The corn oil separated and recovered from the liquefied corn mash contained about 85 wt % glycerides. Most of the balance was free fatty acids.

Example 3

Removal of Corn Oil from Liquefied Corn Mash—Feed Rate Adjustment

In this example, liquefied corn mash was fed to a three-phase centrifuge at a feed rate of 1 gpm. Liquefied corn mash was generated using a standard continuous liquefaction process as used, for example, in a dry-grind corn-to-ethanol process. The ground corn contained 4.16 wt % corn oil (dry corn basis) and had a moisture content of 14.7 wt %. Ground corn and water were fed to a slurry tank at 8.2 lbm/min and 19.0 lbm/min, respectively, to give a dry corn loading of approximately 26 wt %. Alpha-amylase was fed to the slurry tank at a rate of 50 g/hr, which corresponded to an enzyme loading of about 0.026 wt % on a dry corn basis. The slurry and liquefaction tanks were both run at 85° C. and pH of 5.8. The total residence time at 85° C. was about 2 hr. Mash was produced at a rate of about 3 gpm and stored in a 1500 gal tank. The mash contained about 1.1 wt % corn oil on a wet basis. A portion of this oil existed as free oil and a portion was in the undissolved solids. This corresponds to a total corn oil content of the mash to be about 2.0 lbm of corn oil/bushel of corn. The TS in the mash was 25.6 wt % and the TSS was 5.3 wt %.

The liquefied corn mash was fed from a feed tank to a three-phase centrifuge (Model Z23-3, Flottweg Tricanter®, Flottweg AG, Vilsibiburg, Germany) at a rate of about 1 gpm. The feed temperature was about 80° C. The mash was separated into three streams: (1) corn oil, (2) aqueous solution of oligosaccharides (liquefied starch), and (3) wet cake. The operating conditions of the three-phase centrifuge were as follows:
   Bowl Speed: 5000 rpm
   G-force: 3200 g
   Differential speed: 12 rpm
   Impeller setting: approximately 156
   Phase separator disk: approximately 140 mm Table 5 summarizes data (flow rate, density, solids content, and corn oil content) measured for the feed stream and the three exit streams from the three-phase centrifuge. The quality of the corn oil mass balance was 102% and the quality of the total solids mass balance was 105%.

TABLE 5

|  | Feed Mash | Aqueous Centrate | Wet Cake | Corn Oil |
|---|---|---|---|---|
| Flow Rate, lbm/min: | 9.2 | 6.2 | 3.0 | 0.016 |
| Density, g/ml: | ~1.10 | ~1.09 |  | ~0.9 |
| Total Solids, wt %: | 25.6 | 21.6 | 37.4 | ~0 |
| Total Suspended Solids, wt %: | 5.3 | 1.1 | 13.8 | ~0 |
| Corn Oil Content (wet basis), wt %: | 1.1 | 0.28 | 2.2 | >99 * |
| Corn Oil Content, lbm/bushel: | 2.0 | 0.36 | 1.34 | 0.34 |
| % of the Corn Oil in the feed: | NA | 18 | 67 | 17 |

* Balance is water

The corn oil removed from the mash by the three-phase centrifuge accounted for about 17% of the total corn oil in the mash feed. This corn oil removal rate was equal to about 0.34 lbm/bushel of corn. The corn oil separated and recovered from the liquefied corn mash contained about 81.4 wt % glycerides and about 8.3 wt % free fatty acids.

Example 4

Removal of Corn Oil from Liquefied Corn Mash—Feed Rate Adjustment

In this example, liquefied corn mash was fed to a three-phase centrifuge at a feed rate of 10.1 gpm. Liquefied corn mash was generated using a standard continuous liquefaction process as used, for example, in a dry-grind corn-to-ethanol process. The ground corn contained 4.16 wt % corn oil (dry corn basis) and had a moisture content of 14.7 wt %. Ground corn and water were fed to a slurry tank at 8.2 lbm/min and 19.0 lbm/min, respectively, to give a dry corn loading of approximately 26 wt %. Alpha-amylase was fed to the slurry tank at a rate of 50 g/hr, which corresponded to an enzyme loading of about 0.026 wt % on a dry corn basis. The slurry and liquefaction tanks were both run at 85° C. and pH of 5.8. The total residence time at 85° C. was about 2 hr. Mash was produced at a rate of about 3 gpm and stored in a 1500 gal tank. The mash contained about 1.1 wt % corn oil on a wet basis. A portion of this oil existed as free oil and a portion was in the undissolved solids. This corresponds to a total corn oil content of the mash to be about 2.0 lbm of corn oil/bushel of corn. The TS in the mash was 26.2 wt % and the TSS was 6.7 wt %.

The liquefied corn mash was fed from the feed tank to a three-phase centrifuge (Model Z23-4/441, Flottweg Tricanter®, Flottweg AG, Vilsibiburg, Germany) at a rate of about 10.1 gpm. The feed temperature was about 80° C. The mash was separated into three streams: (1) corn oil, (2) aqueous solution of oligosaccharides (liquefied starch), and (3) wet cake. The operating conditions of the three-phase centrifuge were as follows:

Bowl Speed: 5000 rpm
G-force: 3200 g
Differential speed: 20 rpm
Impeller setting: approximately 148 mm
Phase separator disk: approximately 138 mm Table 6 summarizes data (flow rate, density, solids content, and corn oil content) measured for the feed stream and the three exit streams from the three-phase centrifuge. The quality of the corn oil mass balance was 95%.

TABLE 6

|  | Feed Mash | Aqueous Centrate | Wet Cake | Corn Oil |
|---|---|---|---|---|
| Flow Rate, lbm/min: | 92.2 | 73.1 | 18.9 | 0.177 |
| Density, g/ml: | ~1.10 | ~1.09 |  | ~0.9 |
| Total Solids, wt %: | 26.2 | 23.3 | 36.9 | ~0 |
| Total Suspended Solids, wt %: | 6.7 | 1.9 | 25.2 | ~0 |
| Corn Oil Content (wet basis), wt %: | 1.1 | 0.71 | 1.4 | >99 * |
| Corn Oil Content, lbm/bushel: | 2.0 | 1.02 | 0.52 | 0.36 |
| % of the Corn Oil in the feed: | NA | 51 | 26 | 18 |

* Balance is water

The corn oil removed from the mash by the three-phase centrifuge accounted for about 18% of the total corn oil in the mash feed. This corn oil removal rate was equal to about 0.36 lbm/bushel of corn. The corn oil separated and recovered from the liquefied corn mash contained about 81.4 wt % glycerides and about 8.3 wt % free fatty acids.

Example 5

Recovery of Corn Oil from Corn Mash

Liquefied corn mash was generated using a standard continuous liquefaction process as typically used in a dry-grind corn-to-ethanol process. The ground corn contained 4.6 wt % corn oil (dry corn basis) and had a moisture content of 12.5 wt %. Ground corn and water were fed to a slurry tank at rates to produce corn mash at 3 gpm with a dry corn loading of 25.9 wt %. The slurry tank was operated at 85° C. with a 30 min residence time. The slurry was then heated to 105° C. using live steam in a jet cooker and held at that temperature for about 30 min. After exiting the hold tube, the slurry was fed to a liquefaction tank which was operated at 85° C. with a 90 min residence time. Alpha-amylase (Spezyme® ALPHA, Genencor®, Palo Alto, Calif.) was continuously fed to the process at a rate that corresponded to an overall enzyme loading of 0.04 wt % enzyme on a dry corn basis. Forty percent (40%) of the total enzyme was added to the slurry tank, and 60% was added to the liquefaction tank. The slurry and liquefaction tanks were both run at pH of 5.8. Mash was produced at a rate of about 3 gpm and stored in a 1500 gal tank. The liquefied corn mash contained about 1.12 wt % corn oil on a wet basis. This corresponds to a total corn oil content of the mash to be about 2.2 lbm of corn oil/bushel of corn. Some of this oil existed as free oil; some was in the undissolved solids. The ratio of glycerides to free fatty acids in the corn oil in the mash was about 7.6 to 1. The total solids (TS) in the mash were 25.9 wt %, and the total suspended solids (TSS) were 4.7 wt %. The DE (dextrose equivalent) and the pH of the final mash was 15.9 and 5.75, respectively. The density of the mash was 1.08 g/mL.

The liquefied mash was separated using a three-phase centrifuge (Model Z23-4/441, Flottweg Tricanter®, Flottweg AG, Vilsibiburg, Germany) at three different feed flow rates: 1.24 gal/min, 5.1 gal/min, and 10 gal/min. The feed temperature was about 80° C. The mash was separated into three streams: (1) corn oil, (2) aqueous solution of oligosaccharides (liquefied starch), and (3) wet cake. The bowl speed was held constant at about 5000 rpm (approximately 4000 g). Table 7 compares the corn oil recovery as a function of mash feed rate to the three-phase centrifuge for a mash pH of 5.8. The data shown in Table 7 shows that there is an effect of feed rate to the three-phase centrifuge on the recovery rate of corn oil at pH=5.8.

TABLE 7

| Test | Mash Feed Rate, gpm | Differential Speed, rpm | Impeller Setting, mm | Corn Oil in Mash, g/min | Corn Oil Recovered, g/min | Corn Oil Recovery % |
|---|---|---|---|---|---|---|
| A | 1.2 | 5.2 | 144 | 63.3 | 8.3 | 13 |
| B | 5.1 | 10.5 | 146 | 248.4 | 73.2 | 29 |
| C | 10 | 9.8 | 149 | 487.1 | 100.3 | 21 |

Corn oil recovery is based on the total oil contained in the mash (both free oil and oil in the solids). The mash fed to the three-phase centrifuge contained 1.1-1.2 wt % corn oil (includes free oil and oil in the solids).

The data in Table 7 shows that there is an effect of mash feed rate on corn oil recovery rate (at the conditions tested). Table 8 summarizes the amount of oil phase in the aqueous centrate, aqueous phase in the oil centrate, and solids in the oil centrate for the three conditions tested.

TABLE 8

| Test | Mash Feed Rate, gpm | Corn Oil Recovery % | Corn Oil in Aqueous Centrate, vol %* | Aqueous Phase in Corn Oil, vol %* | Solids in Corn Oil, vol %* | Density of Corn Oil, g/mL |
|---|---|---|---|---|---|---|
| A | 1.2 | 13 | 0 | 0 | 1.8 | 0.892 |
| B | 5.1 | 29 | 0 | 0 | 1.7 | 0.892 |
| C | 10 | 21 | 0 | 3 | 1.5 | 0.906 |

*Measured using a LuMiSizer ® (L.U.M. GmbH, Berlin, Germany)

The data in Table 8 shows that the corn oil recovered was fairly clean since it contained very little aqueous phase and very little solids. The corn oil separated and recovered from the liquefied corn mash contained about 85.1 wt % glycerides and about 8.0 wt % free fatty acids. The balance was solids, aqueous phase, and other extractables (e.g., phospholipids, sterols, etc,).

Example 6

Recovery of Corn Oil and Solids from Corn Mash

Liquefied corn mash was generated using a standard continuous liquefaction process as used in a dry-grind corn-to-ethanol process with 30-31 wt % on a dry corn basis. Recycle water consisting of cook water and backset was used, which elevated the total solids (TS) to approximately 33 wt %. Alpha-amylase (Spezyme® RSL, Genencor®, Palo Alto, Calif.) was added to the slurry tank (85° C., pH approximately 5.8, 30 min residence time) at a rate that corresponded to approximately 0.02 wt % dry corn base enzyme load. A jet cooker was used to elevate the temperature to 105-110° C. with 18 min cook time. The liquefaction tank was run at 85° C. with a pH of approximately 5.8. Spezyme® RSL (Genencor®, Palo Alto, Calif.) was also added to the liquefaction tank at a rate that corresponded to approximately 0.005 wt % dry corn base enzyme load, and the total residence time in the liquefaction tank was about 90 min. A side stream of mash was collected from the liquefaction tank and diverted to a small dilution tank, where process condensate was added to achieve the desired dilution. The original mash contained about 1.55 wt % corn oil on a wet basis. A portion of this oil existed as free oil and a portion was in the undissolved solids. This corresponds to a total corn oil content of the original mash to be about 3.0 lbm of corn oil/bushel of corn. The TS in the original mash was 33.2 wt % and the total suspended solids (TSS) was 6.5 wt %. The dilution with process condensate lowered the TS to approximately 27 wt %, the TSS to approximately 5.5 wt %, and the oil content to approximately 1.3 wt % (wet basis).

The liquefied corn mash was fed from the feed tank to a three-phase centrifuge (Model Z23-4/441, Flottweg Tricanter®, Flottweg AG, Vilsibiburg, Germany) at a rate between 9 and 11 gpm. The feed temperature was about 85° C. The mash was separated into three streams: (1) corn oil, (2) aqueous solution of oligosaccharides (liquefied starch), and (3) wet cake. The operating conditions of the three-phase centrifuge were as follows:

Bowl Speed: 5000 rpm
G-force: approximately 3200 g
Differential speed: 25 rpm
Impeller setting: see Table 9
Phase separator disk: approximately 138 mm Table 9 summarizes three-phase centrifuge conditions and properties following separation. Streams at both corn loads 33 wt % and 26 wt % were separated into a very clean corn oil stream and wet cake at about 38-41 wt % total solids. The suspended solids concentration in the heavy phase was strongly affected by the corn load. The 33 wt % sample generated a centrate TSS of about 3.5-4 wt %, while the 26 wt % TS generated a lower TSS centrate at about 1.7-2 wt %.

TSS was about 3.3%, and the centrate TSS increased to about 4.2-4.7% with a flow rate of 11.5 gpm.

Figure 6A:
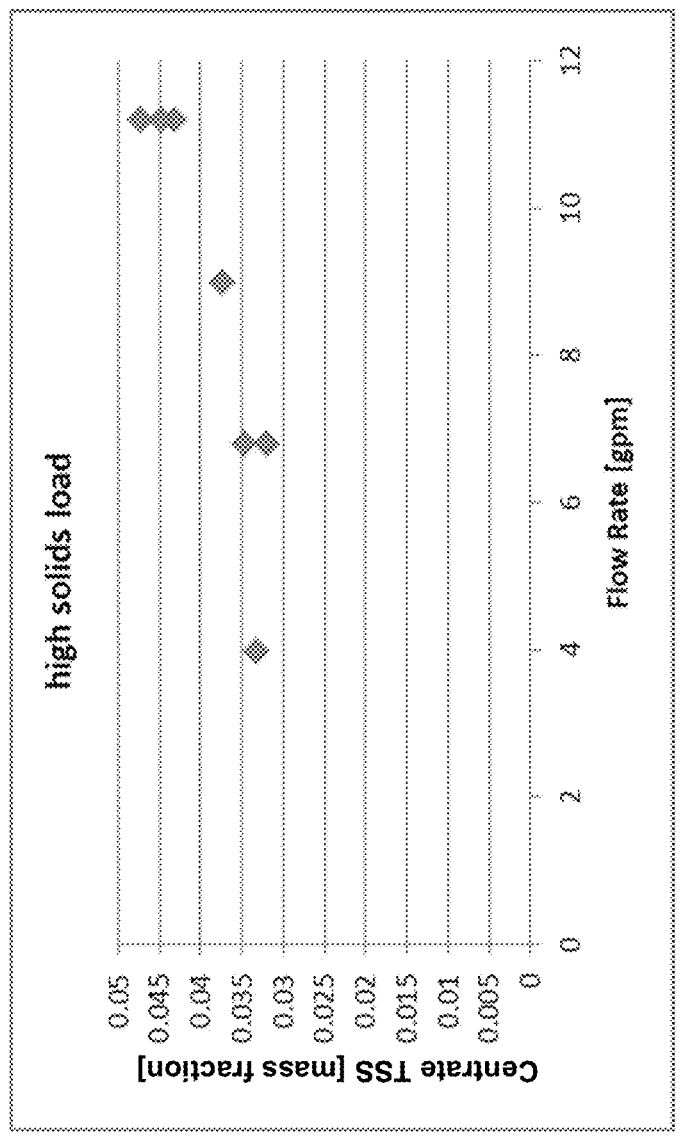
FIGS. 6A-6F illustrate the effect of three-phase centrifuge conditions on separation of feedstock slurry.
Figure 6B:
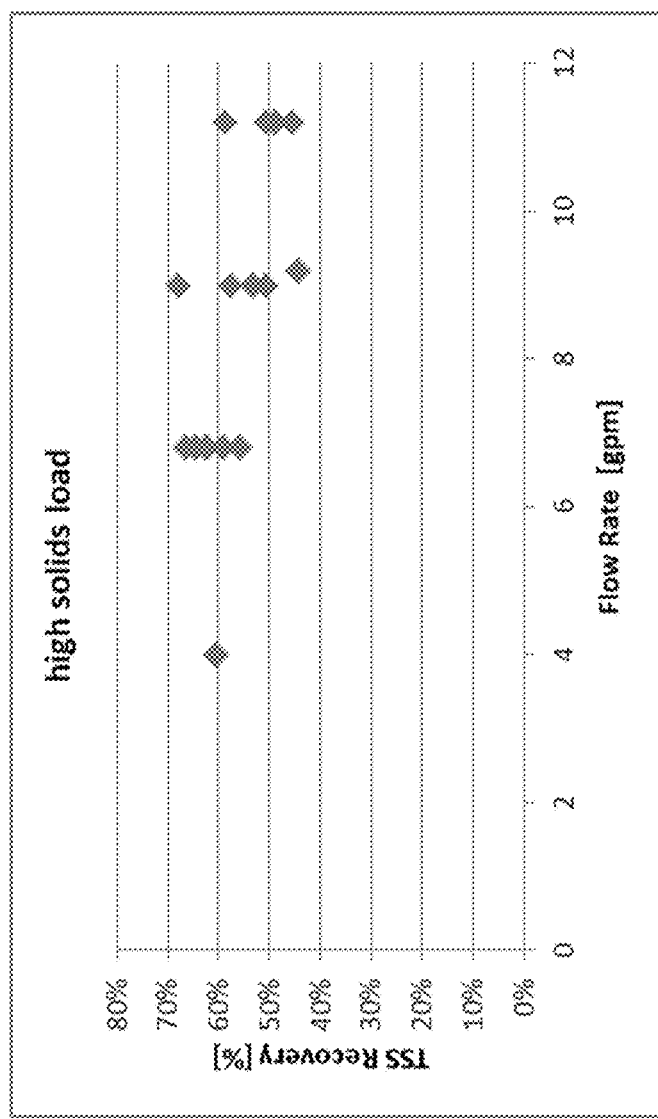

FIG. 6B shows the suspended solids recovery as a function of flow rate. At low flow rates of approximately 4 gpm, approximately 60% of the suspended solids were recovered in the wet cake. By increasing the flow rate to about 11.5 gpm, the recovery rate decreased to about 40-50%.

Figure 6C:
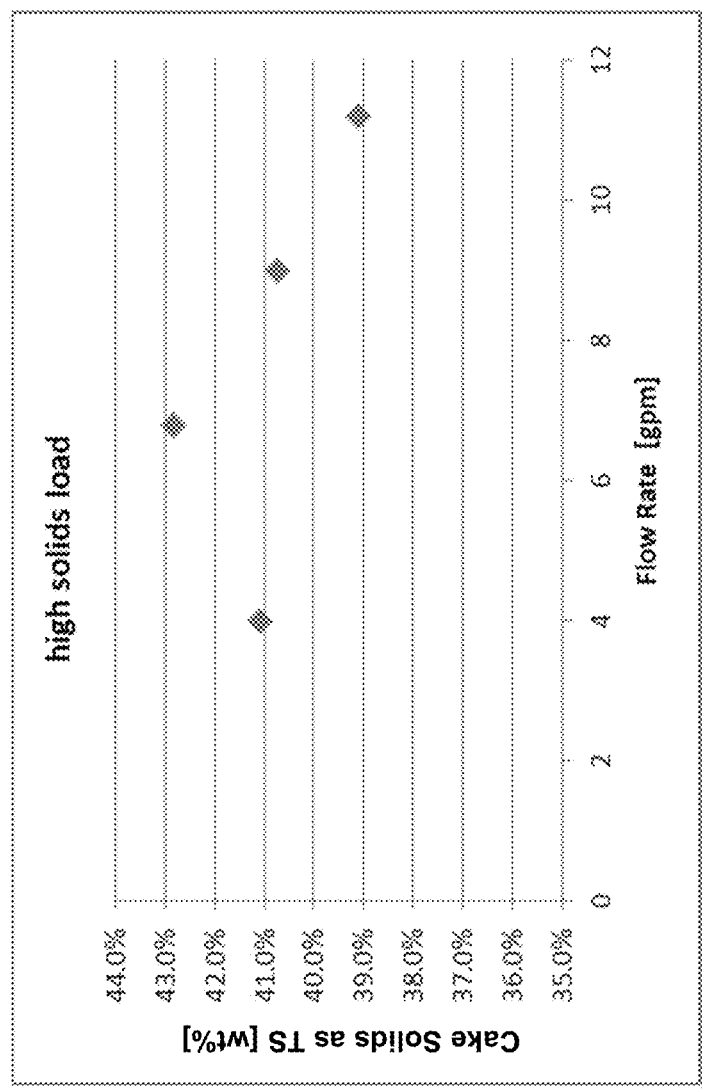

FIG. 6C shows the wet cake total solids as a function of flow rate. At low flow rates of approximately 4 gpm, wet cake total solids were about 41%. By increasing the flow rate to about 11.5 gpm, the wet cake total solids decreased to about 39%.

Figure 6D:
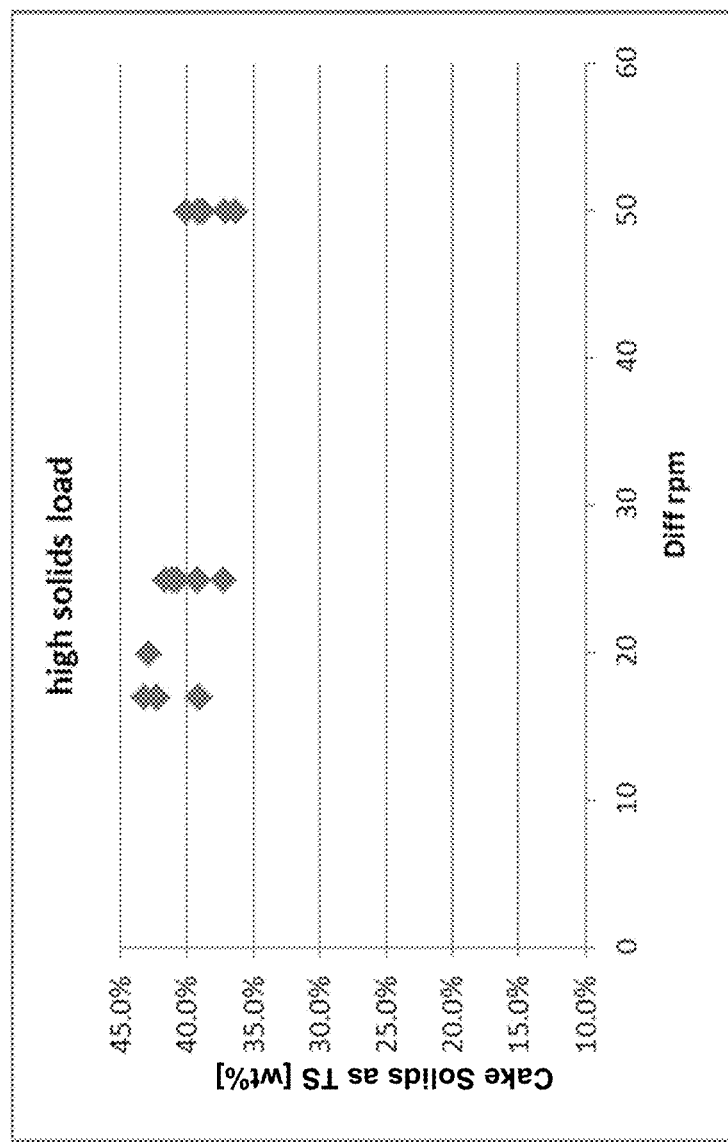

FIG. 6D shows the impact of differential rpm on the total wet cake solids. The wet cake solids decreased with increased differential rpm.

Figure 6E:
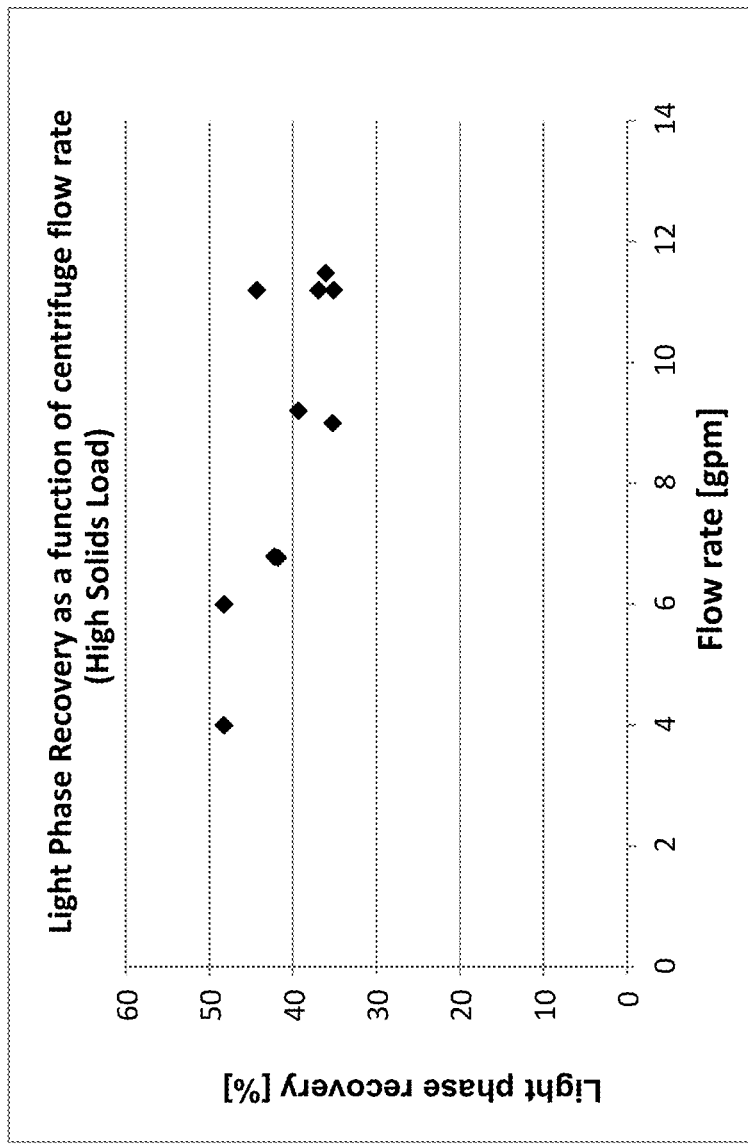

FIG. 6E shows the effect of feed rate on corn oil recovery (i.e., light phase recovery). At low flow rates, oil recovery was about 48%. When the flow rate was increased to approximately 11.5 gpm, oil recovery decreases to about 35%. It appears that less oil is separated from the feed stream with higher flow rate.

Figure 6F:
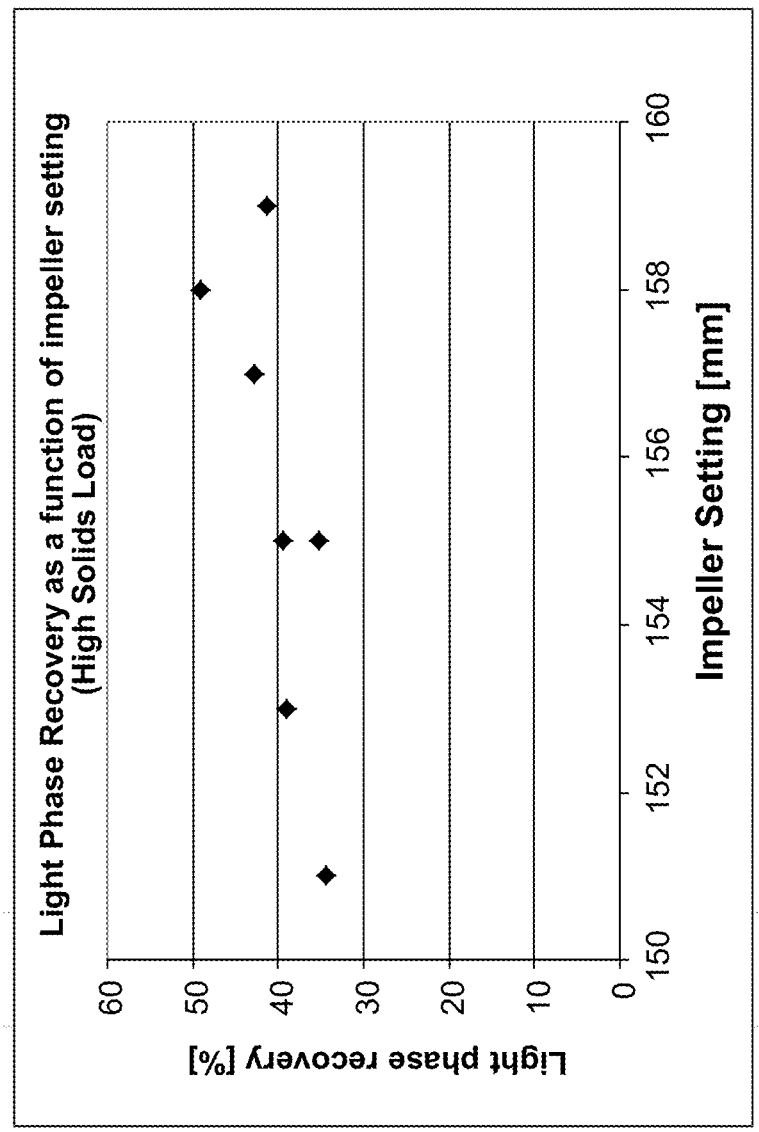

FIG. 6F shows the effect of the impeller setting on corn oil recovery. At low impeller settings (e.g., 151 mm), about 35% of the incoming oil was recovered. By increasing the impeller setting (e.g., 159 mm), oil recovery was improved to about 40-50%.

Example 7

Recovery of Corn Oil and Undissolved Solids from Corn Mash

Liquefied corn mash was generated using a standard continuous liquefaction process as used in a dry-grind corn-to-ethanol process with 30-31 wt % on a dry corn basis. Recycle water consisting of cook water and backset were used, which elevated the total solids (TS) to approximately 33 wt %. Alpha-amylase (Spezyme® RSL, Genencor®, Palo Alto, Calif.) was added to the slurry tank (85° C., pH approximately 5.8, 30 min residence time) at a rate that corresponded to approximately 0.02 wt % dry corn base enzyme load. A jet cooker was used to elevate the temperature to 105-110° C. with an 18 min cook time. The lique-

TABLE 9

| Feed Properties | | | | |
|---|---|---|---|---|
| TS (wt %) | 33 | 33 | 26 | 26 |
| Feed rate (gpm) | 9 | 11.2 | 9 | 11.3 |
| Centrifuge Conditions | | | | |
| Bowl speed (rpm) | 5000 | 5000 (4400-5400) | 5000 | 5000 |
| Differential speed (rpm) | 25 (25-50) | 25 (25-50) | 25 | 15 (15-25) |
| Impeller Speed (mm) | 155 (145-158) | 155 (155-160) | 155 | 153 (153-155) |
| Light Centrate Properties | | | | |
| Water content (ppm) | Very low | Very low | Very low | Very low |
| TSS (wt %) | Very low | Very low | Very low | Very low |
| Flow rate (mL/min) | 230 (150-330) | 300 (195-360) | 280 (170-280) | 364 (364-459) |
| Recovery (on total basis) (%) | 43 (30-60) | 43 (30-54) | 53 (30-53) | 54 (54-68) |
| Heavy Centrate Properties | | | | |
| TSS (wt %) | 3.5 (3.5-4) | 4.3 (3.6-4.7) | 1.7 (1.7-3.8) | 2 (2-3.2) |
| Wet Cake Properties | | | | |
| TS (wt %) | 41 (36-42) | 39 (37-39) | 38.7 (38.5-38.7) | 39 (30-40) |

Results are also shown in FIGS. 6A to 6F. FIG. 6A shows that at low flow rates of approximately 4 gpm, the centrate faction tank was run at 85° C. and a pH of approximately 5.8. Spezyme® RSL (Genencor®, Palo Alto, Calif.) was also added to the liquefaction tank at a rate that corresponded to approximately 0.005 wt % dry corn base enzyme load, and the total residence time in the liquefaction tank was about 90 min. A side stream of mash was collected from the liquefaction tank and diverted to a small tank that served as feed tank to the centrifuge. The mash contained about 1.5 wt % corn oil on a wet basis. A portion of this oil existed as free oil and a portion was in the undissolved solids. This corresponds to a total corn oil content of the mash to be about 3.0 lbm of corn oil/bushel of corn. The TS in the original mash was 33.1 wt % and the TSS was 6.5 wt %.

The liquefied corn mash was fed from the feed tank to a three-phase centrifuge (Model Z4-4/441, Flottweg Tricanter®, Flottweg AG, Vilsibiburg, Germany) at a rate between 40 and 75 gpm. The feed temperature was about 85° C. The mash was separated into three streams: (1) corn oil, (2) aqueous solution of oligosaccharides (liquefied starch), and (3) wet cake. The operating conditions of the three-phase centrifuge were as follows:
  Bowl Speed: 3650 rpm
  G-force: approximately 3200 g
  Differential speed: 15-25 rpm
  Impeller setting: 265-275 mm
  Phase separator disk: approximately 242 mm Table 10 summarizes three-phase centrifuge conditions and properties following separation. The liquefied mash at 33 wt % corn load was separated into a very clean corn oil stream and wet cake at about 42-47 wt % total solids. The suspended solids concentration in the heavy phase was strongly affected by the flow rate. At 43 gpm feed flow, thin mash with about 3.5 wt % TSS was produced; at 61 gpm, thin mash with about 3.9 wt % TSS was produced; and at 75 gpm, thin mash with about 4.7 wt % TSS was produced. The free fatty acid (FFA) content of the corn oil stream was about 10.3 wt % (<15%) and the Moisture, Insoluble impurities, and Unsaponifiable matter in the oil (MUI) was about 1.27% (<3%). In addition, the moisture content of the oil was less than 1% as measured by Fourier transform infrared spectroscopy (FTIR), indicating an improved oil quality.

TABLE 10

| Centrifuge | Corn Load (% TS) | Feed Flow Rate (gpm) | Wet Cake (% TS) | Thin Mash (% TSS) | Corn Oil Rate (mL/min) | Corn Oil Moisture Content (% Moisture) |
| --- | --- | --- | --- | --- | --- | --- |
| Z4-4 (3650 rpm) | 34 | 43 | 43 | 3.5 | 1235 | 0.12-0.26 |
|  | 34 | 61 | 47 | 3.9 | 1436 | 0.1-0.68 |
|  | 34 | 75 | 42 | 4.7 | 1425 | 0.27-0.29 |

Example 8

Recovery of Corn Oil and Solids from Corn Mash in Batch Mode

Liquefied corn mash was generated using a standard continuous liquefaction process as typically used in a dry-grind corn-to-ethanol process. Ground corn and water were fed to a slurry tank at rates to produce corn mash at 3 gpm with a dry corn loading of 33 wt %. The slurry tank was operated at 85° C. with a 30 min residence time. The slurry was then heated to 105° C. using live steam in a jet cooker and held at that temperature for about 30 min. After exiting the hold tube, the slurry was fed to a liquefaction tank which was operated at 85° C. with a 90 min residence time. Alpha-amylase (Spezyme® CL, Genencor®, Palo Alto, Calif.) was continuously fed to the process at a rate that corresponded to an overall enzyme loading of 0.04 wt % enzyme on a dry corn basis. Forty percent (40%) of the total enzyme was added to the slurry tank, and 60% was added to the liquefaction tank. The slurry and liquefaction tanks were both run at pH of 5.8. Mash was produced at a rate of about 3 gpm and stored in a 1500 gal tank. The liquefied corn mash contained about 1.5 wt % corn oil on a wet basis. This corresponds to a total corn oil content of the mash to be about 3 lbm of corn oil/bushel of corn. Some of this oil existed as free oil; some was in the undissolved solids. The total solids (TS) in the mash were 33 wt %, and the total suspended solids (TSS) were 6.5 wt %.

Figure 7:
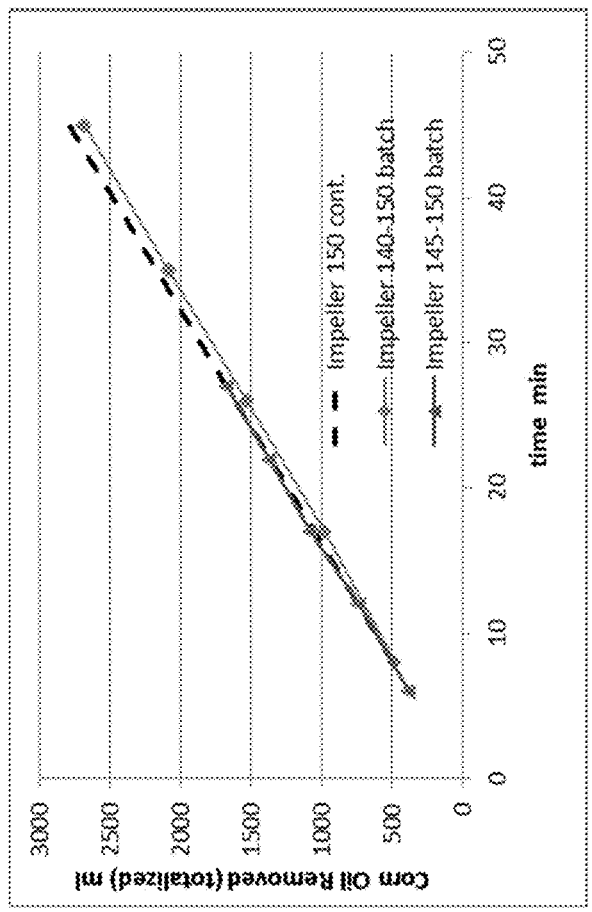
FIG. 7 illustrates the effect of three-phase centrifuge conditions on batch mode oil recovery.

The liquefied corn mash was fed from the feed tank to a three-phase centrifuge (Model Z23-4/441, Flottweg Tricanter®, Flottweg AG, Vilsibiburg, Germany) at a rate of 4.3 gpm. The feed temperature was about 85° C. The mash was separated into three streams: (1) corn oil, (2) aqueous solution of oligosaccharides (liquefied starch), and (3) wet cake. The impeller was set initially at a high diameter to allow the light oil phase to accumulate inside the centrifuge. At this point, no oil was discharged from the light phase outlet. Upon the first oil discharge, the impeller was lowered to a smaller diameter to discharge the accumulated corn oil. The impeller was set back to a high diameter to accumulate oil again. The operating conditions of the three-phase centrifuge were as follows:
  Bowl Speed: 5000 rpm
  G-force: approximately 3200 g
  Differential speed: 25 rpm
  Impeller setting: 140-150 mm
  Phase separator disk: approximately 138 mm FIG. 7 illustrates the results for batch mode oil recovery. The solid lines represent intermittent oil removal rate and the dashed line represents continuous oil removal. Equal amounts of oil were recovered by both methods. During intermittent removal, the residence time of the oil is prolonged, potentially leading to less suspended solids and aqueous phase in the oil.

While various embodiments of the present invention have been described herein, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:
1. A method for producing product alcohol comprising:
  providing a feedstock slurry comprising fermentable carbon source, undissolved solids, and oil;
  separating at least a portion of the feedstock slurry forming (i) an aqueous solution comprising fermentable carbon source, (ii) a wet cake comprising solids, and (iii) an oil stream; wherein the step of separating at least a portion of the feedstock slurry includes using a three-phase centrifuge to separate the feedstock slurry;

returning at least a portion of the oil stream to the three-phase centrifuge; and adding the aqueous solution to a fermentation broth comprising microorganisms in a fermentor whereby a product alcohol is produced.

2. The method of claim 1, wherein the three-phase centrifuge comprises an overflow mechanism.

3. The method of claim 2, wherein the overflow mechanism is adjustable.

4. The method of claim 2, wherein the overflow mechanism is a weir.

5. The method of claim 2, wherein the overflow mechanism is used for discharging the oil stream.

6. The method of claim 2, wherein the overflow mechanism is used for discharging the aqueous solution.

7. The method of claim 1, wherein the three-phase centrifuge comprises a pressure discharge mechanism.

8. The method of claim 6, wherein the pressure discharge mechanism is adjustable.

9. The method of claim 6, wherein the pressure discharge mechanism is selected from the group consisting of a dip tube and an impeller.

10. The method of claim 6, wherein the pressure discharge mechanism is used for discharging the aqueous solution.

11. The method of claim 6, wherein the pressure discharge mechanism is used for discharging the oil stream.

12. The method of claim 1, wherein one or more control parameters of the three-phase centrifuge is adjusted to improve separation of the feedstock slurry.

13. The method of claim 12, wherein the one or more control parameters are selected from differential speed, bowl speed, flow rate, impeller position, weir position, scroll pitch, residence time, and discharge volume.

14. The method of claim 1, wherein the oil stream is separated from the feedstock slurry intermittently.

15. The method of claim 1, wherein the oil stream is separated from the feedstock slurry in batch mode.

16. The method of claim 1, further comprising the step of washing the wet cake to recover oil and fermentable sugars.

17. The method of claim 16, wherein the wet cake is washed with water, hexane, isobutanol, isohexane, ethanol, petroleum distillates, or mixtures thereof.

18. The method of claim 17, wherein the water is fresh water, backset, cook water, process water, lutter water, evaporation water, or combinations thereof.

19. The method of claim 16, wherein the washing step is repeated two or more times.

20. The method of claim 1, further comprising recombining at least a portion of the aqueous solution with at least a portion of the wet cake to form a mixture of wet cake and aqueous solution; and adding the mixture to the fermentation broth.

21. The method of claim 1, wherein the product alcohol is methanol, ethanol, propanol, butanol, pentanol, and isomers thereof.

22. The method of claim 21, wherein butanol is 1-butanol, 2-butanol, or isobutanol.

23. The method of claim 1, wherein the feedstock slurry comprises oil in an amount that is less than about two volume percent of the feedstock slurry.

24. The method of claim 1, wherein the feedstock slurry comprises oil in an amount that is less than about one volume percent of the feedstock slurry.

25. The method of claim 1, further comprising liquefying a feedstock to create a feedstock slurry.

26. The method of claim 25, wherein the feedstock is rye, wheat, corn, corn mash, cane, cane mash, barley, cellulosic material, lignocellulosic material, or mixtures thereof.

27. The method of claim 1, further comprising separating the aqueous solution forming (i) a second aqueous solution comprising fermentable carbon source, (ii) a second wet cake comprising solids, and (iii) a second oil stream.

28. The method of claim 27, wherein the aqueous solution is separated by decanter bowl centrifugation, three-phase centrifugation, disk stack centrifugation, filtering centrifugation, decanter centrifugation, filtration, microfiltration, vacuum filtration, beltfilter, pressure filtration, membrane filtration, crossflow filtration, drum filter, filtration using a screen, screen separation, rotary screen, grating, porous grating, flotation, hydrocyclone, filter press, screwpress, gravity settler, or vortex separator.

29. A method to improve oil recovery from a feedstock slurry comprising:

providing a feedstock slurry comprising fermentable carbon source, undissolved solids, and oil;

separating at least a portion of the feedstock slurry forming (i) an aqueous solution comprising fermentable carbon source, (ii) a wet cake comprising solids, and (iii) an oil stream; and returning at least a portion of the oil stream to the feedstock slurry;

wherein an increased concentration of oil in the feedstock slurry improves the recovery of oil from the feedstock slurry.

30. A method for producing product alcohol comprising:

providing a feedstock slurry comprising fermentable carbon source, undissolved solids, and oil;

separating at least a portion of the feedstock slurry forming (i) an aqueous solution comprising fermentable carbon source, (ii) a wet cake comprising solids, and (iii) an oil stream; wherein the step of separating at least a portion of the feedstock slurry includes using a three-phase centrifuge to separate the feedstock slurry;

combining the oil stream with feedstock slurry to form a mixture of oil and feedstock slurry;

returning the mixture to the three-phase centrifuge; and adding the aqueous solution to a fermentation broth comprising microorganisms in a fermentor whereby a product alcohol is produced.

31. The method of claim 30, wherein the three-phase centrifuge comprises an overflow mechanism.

32. The method of claim 31, wherein the overflow mechanism is adjustable.

33. The method of claim 31, wherein the overflow mechanism is a weir.

34. The method of claim 31, wherein the overflow mechanism is used for discharging the oil stream or discharging the aqueous solution.

35. The method of claim 1, wherein the three-phase centrifuge comprises a pressure discharge mechanism.

36. The method of claim 35, wherein the pressure discharge mechanism is adjustable.

37. The method of claim 35, wherein the pressure discharge mechanism is selected from the group consisting of a dip tube and an impeller.

38. The method of claim 35, wherein the pressure discharge mechanism is used for discharging the aqueous solution or discharging the oil stream.

39. The method of claim 30, wherein one or more control parameters of the three-phase centrifuge is adjusted to improve separation of the feedstock slurry.

40. The method of claim 39, wherein the one or more control parameters are selected from differential speed, bowl speed, flow rate, impeller position, weir position, scroll pitch, residence time, and discharge volume.

41. The method of claim 30, wherein the oil stream is separated from the feedstock slurry intermittently.

42. The method of claim 30, wherein the oil stream is separated from the feedstock slurry in batch mode.

43. The method of claim 30, further comprising the step of washing the wet cake to recover oil and fermentable sugars.

44. The method of claim 43, wherein the wet cake is washed with water, hexane, isobutanol, isohexane, ethanol, petroleum distillates, or mixtures thereof.

45. The method of claim 30, further comprising recombining at least a portion of the aqueous solution with at least a portion of the wet cake to form a mixture of wet cake and aqueous solution; and adding the mixture to the fermentation broth.

46. The method of claim 1, wherein the product alcohol is methanol, ethanol, propanol, butanol, pentanol, and isomers thereof.

47. The method of claim 46, wherein butanol is 1-butanol, 2-butanol, or isobutanol.

48. The method of claim 30, further comprising separating the aqueous solution forming (i) a second aqueous solution comprising fermentable carbon source, (ii) a second wet cake comprising solids, and (iii) a second oil stream.

49. The method of claim 48, wherein the aqueous solution is separated by decanter bowl centrifugation, three-phase centrifugation, disk stack centrifugation, filtering centrifugation, decanter centrifugation, filtration, microfiltration, vacuum filtration, beltfilter, pressure filtration, membrane filtration, crossflow filtration, drum filter, filtration using a screen, screen separation, rotary screen, grating, porous grating, flotation, hydrocyclone, filter press, screwpress, gravity settler, or vortex separator.

* * * * *